(12) United States Patent
Radovic-Moreno et al.

(10) Patent No.: US 8,193,334 B2
(45) Date of Patent: Jun. 5, 2012

(54) POLYMER-ENCAPSULATED REVERSE MICELLES

(75) Inventors: Aleksandar F. Radovic-Moreno, Cambridge, MA (US); Liangfang Zhang, San Diego, CA (US); Robert S. Langer, Newton, MA (US); Omid C. Farokhzad, Chestnut Hill, MA (US)

(73) Assignees: The Brigham and Women's Hospital, Boston, MA (US); Massachusetts Institute of Technologoy, Cambridge, MA (US)

( * ) Notice: Subject to any disclaimer, the term of this patent is extended or adjusted under 35 U.S.C. 154(b) by 0 days.

(21) Appl. No.: 12/573,411

(22) Filed: Oct. 5, 2009

(65) Prior Publication Data

US 2010/0196482 A1 Aug. 5, 2010

Related U.S. Application Data

(63) Continuation of application No. PCT/US2008/059483, filed on Apr. 4, 2008.

(60) Provisional application No. 60/910,062, filed on Apr. 4, 2007.

(51) Int. Cl.
*C07H 21/04* (2006.01)
*C07H 21/02* (2006.01)
*C12N 15/63* (2006.01)
*A61K 48/00* (2006.01)
*A61K 43/00* (2006.01)

(52) U.S. Cl. ............ 536/24.5; 536/23.1; 536/24.31; 536/24.33; 435/320.1; 514/44; 424/1.11

(58) Field of Classification Search ............ None
See application file for complete search history.

(56) References Cited

U.S. PATENT DOCUMENTS

| | | | |
|---|---|---|---|
| 4,270,537 A | 6/1981 | Romaine | |
| 4,446,122 A | 5/1984 | Chu et al. | |
| 4,596,556 A | 6/1986 | Morrow et al. | |
| 4,638,045 A | 1/1987 | Kohn et al. | |
| 4,790,824 A | 12/1988 | Morrow et al. | |
| 4,806,621 A | 2/1989 | Kohn et al. | |
| 4,862,851 A | 9/1989 | Washino et al. | |
| 4,886,499 A | 12/1989 | Cirelli et al. | |
| 4,902,615 A | 2/1990 | Freeman et al. | |
| 4,940,460 A | 7/1990 | Casey, I et al. | |
| 4,941,880 A | 7/1990 | Burns | |
| 4,946,929 A | 8/1990 | D'Amore et al. | |
| RE33,405 E | 10/1990 | Chu et al. | |
| 4,970,299 A | 11/1990 | Bazinet et al. | |
| 5,010,167 A | 4/1991 | Ron et al. | |
| 5,015,235 A | 5/1991 | Crossman | |
| 5,019,379 A | 5/1991 | Domb et al. | |
| 5,055,404 A | 10/1991 | Ueda et al. | |
| 5,064,413 A | 11/1991 | McKinnon et al. | |
| 5,093,246 A | 3/1992 | Cech et al. | |
| 5,118,528 A | 6/1992 | Fessi et al. | |
| 5,141,496 A | 8/1992 | Dalto et al. | |
| 5,162,504 A | 11/1992 | Horoszewicz | |
| 5,190,521 A | 3/1993 | Hubbard et al. | |
| 5,270,163 A | 12/1993 | Gold et al. | |
| 5,312,335 A | 5/1994 | McKinnon et al. | |
| 5,328,483 A | 7/1994 | Jacoby | |
| 5,334,144 A | 8/1994 | Alchas et al. | |
| 5,334,497 A | 8/1994 | Inaba et al. | |
| 5,339,163 A | 8/1994 | Homma et al. | |
| 5,342,781 A | 8/1994 | Su | |
| 5,383,851 A | 1/1995 | McKinnon, Jr. et al. | |
| 5,399,665 A | 3/1995 | Barrera et al. | |
| 5,417,662 A | 5/1995 | Hjertman et al. | |
| 5,466,220 A | 11/1995 | Brenneman | |
| 5,472,704 A | 12/1995 | Santus et al. | |
| 5,480,381 A | 1/1996 | Weston | |
| 5,500,161 A | 3/1996 | Andrianov et al. | |
| 5,503,627 A | 4/1996 | McKinnon et al. | |
| 5,512,600 A | 4/1996 | Mikos et al. | |
| 5,514,378 A | 5/1996 | Mikos et al. | |
| 5,520,639 A | 5/1996 | Peterson et al. | |
| 5,527,288 A | 6/1996 | Gross et al. | |
| 5,543,158 A | 8/1996 | Gref et al. | |
| 5,567,588 A | 10/1996 | Gold et al. | |
| 5,569,189 A | 10/1996 | Parsons | |
| 5,578,325 A | 11/1996 | Domb et al. | |
| 5,595,877 A | 1/1997 | Gold et al. | |
| 5,599,302 A | 2/1997 | Lilley et al. | |
| 5,649,912 A | 7/1997 | Peterson | |
| 5,660,985 A | 8/1997 | Pieken et al. | |
| 5,696,175 A | 12/1997 | Mikos et al. | |
| 5,696,249 A | 12/1997 | Gold et al. | |
| 5,704,911 A | 1/1998 | Parsons | |
| 5,716,404 A | 2/1998 | Vacanti et al. | |
| 5,733,925 A | 3/1998 | Kunz et al. | |
| 5,736,372 A | 4/1998 | Vacanti et al. | |
| 5,763,177 A | 6/1998 | Gold et al. | |
| 5,770,417 A | 6/1998 | Vacanti et al. | |
| 5,786,204 A | 7/1998 | He et al. | |
| 5,789,163 A | 8/1998 | Drolet et al. | |
| 5,804,178 A | 9/1998 | Vacanti et al. | |
| 5,817,785 A | 10/1998 | Gold et al. | |

(Continued)

FOREIGN PATENT DOCUMENTS

CA 2649149 10/2007

(Continued)

OTHER PUBLICATIONS

Sarkar et al. (Biopolymers, 2006, 83(6), pp. 675-686).*

(Continued)

*Primary Examiner* — Amy Bowman
(74) *Attorney, Agent, or Firm* — Pabst Patent Group LLP

(57) ABSTRACT

A method for encapsulating nucleic acids, particularly siRNAs, shRNAs, microRNAs, gene therapy plasmids, and other oligonucleotides in biodegradable polymers is disclosed, whereby the nucleic acids are formulated into reverse micelles composed of non-toxic and/or naturally-occurring lipids prior to nanoparticle formation by nanoprecipitation. This method can be coupled to other techniques that improve intracellular drug targeting, ultimately enhancing intracellular delivery of the aforementioned nucleic acids.

25 Claims, 7 Drawing Sheets

U.S. PATENT DOCUMENTS

| | | | |
|---|---|---|---|
| 5,820,879 | A | 10/1998 | Fernandez et al. |
| 5,837,752 | A | 11/1998 | Shastri et al. |
| 5,843,653 | A | 12/1998 | Gold et al. |
| 5,843,732 | A | 12/1998 | Davis et al. |
| 5,853,984 | A | 12/1998 | Davis et al. |
| 5,869,103 | A | 2/1999 | Yeh et al. |
| 5,874,218 | A | 2/1999 | Drolet et al. |
| 5,893,397 | A | 4/1999 | Peterson et al. |
| 5,898,031 | A | 4/1999 | Crooke |
| 5,902,599 | A | 5/1999 | Anseth et al. |
| 5,916,539 | A | 6/1999 | Pilgrimm |
| 5,958,691 | A | 9/1999 | Pieken et al. |
| 5,977,089 | A | 11/1999 | Arimilli et al. |
| 5,993,412 | A | 11/1999 | Deily et al. |
| 6,001,577 | A | 12/1999 | Gold et al. |
| 6,005,087 | A | 12/1999 | Cook et al. |
| 6,007,845 | A | 12/1999 | Domb et al. |
| 6,031,086 | A | 2/2000 | Switzer |
| 6,095,148 | A | 8/2000 | Shastri et al. |
| 6,107,094 | A | 8/2000 | Crooke |
| 6,110,462 | A | 8/2000 | Barbas et al. |
| 6,120,666 | A | 9/2000 | Jacobson |
| 6,123,727 | A | 9/2000 | Vacanti et al. |
| 6,127,533 | A | 10/2000 | Cook et al. |
| 6,184,364 | B1 | 2/2001 | Pieken et al. |
| 6,190,913 | B1 | 2/2001 | Singh |
| 6,225,460 | B1 | 5/2001 | Bischofberger et al. |
| 6,238,705 | B1 | 5/2001 | Liu et al. |
| 6,242,246 | B1 | 6/2001 | Gold et al. |
| 6,254,890 | B1 | 7/2001 | Hirosue et al. |
| 6,344,318 | B1 | 2/2002 | Gold et al. |
| 6,365,187 | B2 | 4/2002 | Mathiowitz et al. |
| 6,376,190 | B1 | 4/2002 | Gold et al. |
| 6,399,754 | B1 | 6/2002 | Cook |
| 6,403,779 | B1 | 6/2002 | Kawasaki et al. |
| 6,429,200 | B1 | 8/2002 | Monahan et al. |
| 6,451,527 | B1 | 9/2002 | Larocca et al. |
| 6,458,539 | B1 | 10/2002 | Gold et al. |
| 6,458,543 | B1 | 10/2002 | Gold et al. |
| 6,482,594 | B2 | 11/2002 | Gold et al. |
| 6,492,554 | B2 | 12/2002 | Dalton et al. |
| 6,506,559 | B1 | 1/2003 | Fire et al. |
| 6,506,577 | B1 | 1/2003 | Deming et al. |
| 6,569,896 | B2 | 5/2003 | Dalton et al. |
| 6,589,562 | B1 | 7/2003 | Shefer et al. |
| 6,589,563 | B2 | 7/2003 | Prokop |
| 6,632,922 | B1 | 10/2003 | Deming et al. |
| 6,686,446 | B2 | 2/2004 | Deming et al. |
| 6,716,583 | B2 | 4/2004 | Gold et al. |
| 6,818,732 | B2 | 11/2004 | Deming et al. |
| 6,838,484 | B2 | 1/2005 | Steiner et al. |
| 6,875,605 | B1 | 4/2005 | Ma |
| 6,932,971 | B2 | 8/2005 | Bachmann et al. |
| 6,995,284 | B2 | 2/2006 | Dalton et al. |
| 6,998,500 | B2 | 2/2006 | Dalton et al. |
| 7,008,411 | B1 | 3/2006 | Mandrusov et al. |
| 7,022,870 | B2 | 4/2006 | Dalton et al. |
| 7,026,500 | B2 | 4/2006 | Dalton et al. |
| 7,029,859 | B2 | 4/2006 | Thompson |
| 7,056,704 | B2 | 6/2006 | Tuschl et al. |
| 7,078,196 | B2 | 7/2006 | Tuschl et al. |
| 7,163,680 | B2 | 1/2007 | Bander |
| 7,550,441 | B2 | 6/2009 | Farkhzad et al. |
| 7,727,969 | B2 | 6/2010 | Farokhzad |
| 2001/0012890 | A1 | 8/2001 | Thompson |
| 2002/0009466 | A1 | 1/2002 | Brayden |
| 2002/0064780 | A1 | 5/2002 | Gold et al. |
| 2002/0068091 | A1 | 6/2002 | Davis et al. |
| 2002/0086356 | A1 | 7/2002 | Tuschl et al. |
| 2002/0099036 | A1 | 7/2002 | Dalton et al. |
| 2002/0099096 | A1 | 7/2002 | Dalton et al. |
| 2002/0102613 | A1 | 8/2002 | Hogenboom |
| 2002/0106647 | A1 | 8/2002 | Segal |
| 2002/0150578 | A1 | 10/2002 | He et al. |
| 2002/0153251 | A1 | 10/2002 | Sassi et al. |
| 2002/0156125 | A1 | 10/2002 | Broder et al. |
| 2002/0173495 | A1 | 11/2002 | Dalton et al. |
| 2003/0003103 | A1 | 1/2003 | Thompson |
| 2003/0009029 | A1 | 1/2003 | Buchholz et al. |
| 2003/0022868 | A1 | 1/2003 | Dalton et al. |
| 2003/0035804 | A1 | 2/2003 | D'Amico et al. |
| 2003/0054360 | A1 | 3/2003 | Gold et al. |
| 2003/0087301 | A1 | 5/2003 | Smith et al. |
| 2003/0108611 | A1 | 6/2003 | Bosch et al. |
| 2003/0108923 | A1 | 6/2003 | Tuschl et al. |
| 2003/0134810 | A1 | 7/2003 | Springate et al. |
| 2003/0138557 | A1 | 7/2003 | Allison |
| 2003/0162761 | A1 | 8/2003 | Steiner et al. |
| 2003/0175950 | A1 | 9/2003 | McSwiggen |
| 2003/0219766 | A1 | 11/2003 | Raitano et al. |
| 2003/0225040 | A1 | 12/2003 | Dalton et al. |
| 2003/0232013 | A1 | 12/2003 | Sieckman et al. |
| 2003/0232792 | A1 | 12/2003 | Dalton et al. |
| 2004/0014975 | A1 | 1/2004 | Dalton et al. |
| 2004/0022840 | A1 | 2/2004 | Nagy et al. |
| 2004/0029913 | A1 | 2/2004 | Dalton et al. |
| 2004/0043923 | A1 | 3/2004 | Parma et al. |
| 2004/0052727 | A1 | 3/2004 | Dalton et al. |
| 2004/0059094 | A1 | 3/2004 | Bachmann et al. |
| 2004/0067196 | A1 | 4/2004 | Brunke et al. |
| 2004/0067503 | A1 | 4/2004 | Tan et al. |
| 2004/0067979 | A1 | 4/2004 | Dalton et al. |
| 2004/0072234 | A1 | 4/2004 | Parma et al. |
| 2004/0087810 | A1 | 5/2004 | Dalton et al. |
| 2004/0092470 | A1 | 5/2004 | Leonard et al. |
| 2004/0136961 | A1 | 7/2004 | Prokop et al. |
| 2004/0147489 | A1 | 7/2004 | Dalton et al. |
| 2004/0147550 | A1 | 7/2004 | Dalton et al. |
| 2004/0156846 | A1 | 8/2004 | Daum et al. |
| 2004/0167103 | A1 | 8/2004 | Dalton et al. |
| 2004/0192626 | A1 | 9/2004 | McSwiggen et al. |
| 2004/0241790 | A1 | 12/2004 | Eriksen et al. |
| 2004/0248088 | A1 | 12/2004 | Raitano et al. |
| 2004/0260092 | A1 | 12/2004 | Miller et al. |
| 2004/0260108 | A1 | 12/2004 | Dalton et al. |
| 2004/0266688 | A1 | 12/2004 | Nayak |
| 2005/0017667 | A1 | 1/2005 | Yamamoto |
| 2005/0019870 | A1 | 1/2005 | Afar et al. |
| 2005/0019872 | A1 | 1/2005 | Afar et al. |
| 2005/0020525 | A1 | 1/2005 | McSwiggen et al. |
| 2005/0032733 | A1 | 2/2005 | McSwiggen et al. |
| 2005/0033074 | A1 | 2/2005 | Dalton et al. |
| 2005/0037075 | A1 | 2/2005 | Farokhzad et al. |
| 2005/0048063 | A1 | 3/2005 | Ruoslahti et al. |
| 2005/0069910 | A1 | 3/2005 | Turner et al. |
| 2005/0080128 | A1 | 4/2005 | Tsukamoto et al. |
| 2005/0100877 | A1 | 5/2005 | Xu et al. |
| 2005/0122550 | A1 | 6/2005 | Plewa et al. |
| 2005/0158390 | A1 | 7/2005 | Rana et al. |
| 2005/0191294 | A1 | 9/2005 | Arap et al. |
| 2005/0233948 | A1 | 10/2005 | D'Amico et al. |
| 2005/0244863 | A1 | 11/2005 | Mir |
| 2005/0249799 | A1 | 11/2005 | Jacob et al. |
| 2005/0260186 | A1 | 11/2005 | Bookbinder et al. |
| 2006/0002852 | A1 | 1/2006 | Saltzman et al. |
| 2006/0004042 | A1 | 1/2006 | Dalton et al. |
| 2006/0009529 | A1 | 1/2006 | Dalton et al. |
| 2006/0035966 | A1 | 2/2006 | Dalton et al. |
| 2006/0062787 | A1 | 3/2006 | Hitraya |
| 2006/0083711 | A1 | 4/2006 | Berry et al. |
| 2006/0173170 | A1 | 8/2006 | Chamberlian et al. |
| 2006/0183931 | A1 | 8/2006 | Dalton et al. |
| 2006/0228371 | A1 | 10/2006 | Raso |
| 2006/0239907 | A1 | 10/2006 | Luzzi et al. |
| 2006/0240093 | A1 | 10/2006 | Maclachlan et al. |
| 2006/0241180 | A1 | 10/2006 | Dalton et al. |
| 2006/0258628 | A1 | 11/2006 | Steiner et al. |
| 2006/0269557 | A1 | 11/2006 | Sherman et al. |
| 2006/0276540 | A1 | 12/2006 | Dalton et al. |
| 2006/0287547 | A1 | 12/2006 | Dalton et al. |
| 2008/0026000 | A1 | 1/2008 | Ennifar |
| 2008/0081074 | A1 | 4/2008 | Gu et al. |
| 2008/0268063 | A1 | 10/2008 | Jon et al. |
| 2008/0299177 | A1* | 12/2008 | Hardy ............................ 424/427 |
| 2009/0028910 | A1 | 1/2009 | DeSimone et al. |
| 2009/0117549 | A1 | 5/2009 | Tan |
| 2009/0298710 | A1 | 12/2009 | Farokhzad et al. |

| | | | |
|---|---|---|---|
| 2010/0022680 | A1 | 1/2010 | Kamik et al. |
| 2010/0092425 | A1 | 4/2010 | Von Andrian et al. |
| 2010/0129392 | A1 | 5/2010 | Shi et al. |
| 2010/0129439 | A1 | 5/2010 | Alexis et al. |
| 2010/0144845 | A1 | 6/2010 | Farokhzad et al. |
| 2010/0183727 | A1 | 7/2010 | Iannaconna et al. |
| 2010/0203142 | A1 | 8/2010 | Zhang et al. |
| 2010/0233251 | A1 | 9/2010 | Von Andrian et al. |

FOREIGN PATENT DOCUMENTS

| | | |
|---|---|---|
| DK | 0418187 | 3/1991 |
| EP | 1752141 | 2/2007 |
| EP | 1932538 | 6/2008 |
| WO | WO 88/04300 | 6/1988 |
| WO | WO 90/11364 | 3/1990 |
| WO | WO 97/04747 | 2/1997 |
| WO | WO 97/13537 | 4/1997 |
| WO | WO 97/37705 | 10/1997 |
| WO | WO 98/08856 | 3/1998 |
| WO | 98/51325 | 11/1998 |
| WO | 99/01498 | 1/1999 |
| WO | WO 99/34850 | 7/1999 |
| WO | WO 00/21572 | 4/2000 |
| WO | WO 00/27363 | 5/2000 |
| WO | WO 00/44895 | 8/2000 |
| WO | WO 01/75164 | 10/2001 |
| WO | WO 02/18477 | 3/2002 |
| WO | WO 02/076469 | 10/2002 |
| WO | WO 02/076603 | 10/2002 |
| WO | WO 02/100442 | 12/2002 |
| WO | WO 03/000777 | 1/2003 |
| WO | WO 03/004654 | 1/2003 |
| WO | WO 03/028657 | 4/2003 |
| WO | WO 03/030941 | 4/2003 |
| WO | WO 03/051304 | 6/2003 |
| WO | WO 03/072637 | 9/2003 |
| WO | WO 03/102708 | 12/2003 |
| WO | 2004030608 | 4/2004 |
| WO | WO 2004/030608 | 4/2004 |
| WO | WO 2004/071493 | 8/2004 |
| WO | WO 2004/096998 | 11/2004 |
| WO | WO 2005/012407 | 2/2005 |
| WO | WO 2005/028539 | 3/2005 |
| WO | WO 2005/042573 | 5/2005 |
| WO | WO 2005/072710 | 8/2005 |
| WO | WO 2005/111192 | 11/2005 |
| WO | WO 2005/121181 | 12/2005 |
| WO | WO 2006/037979 | 4/2006 |
| WO | WO 2006/042146 | 4/2006 |
| WO | WO 2006/066158 | 6/2006 |
| WO | WO 2006/078278 | 7/2006 |
| WO | WO 2006/090924 | 8/2006 |
| WO | WO 2006/096754 | 9/2006 |
| WO | WO 2006/117217 | 11/2006 |
| WO | WO 2006/133271 | 12/2006 |
| WO | WO 2006/138463 | 12/2006 |
| WO | WO 2007/021142 | 2/2007 |
| WO | 2007024026 | 3/2007 |
| WO | WO 2007/070682 | 6/2007 |
| WO | WO 2007/076371 | 7/2007 |
| WO | WO 2007/084797 | 7/2007 |
| WO | WO 2007/109364 | 9/2007 |
| WO | WO 2007/118653 | 10/2007 |
| WO | WO 2007/150030 | 12/2007 |
| WO | WO 2008/051291 | 5/2008 |
| WO | WO 2009/051837 | 4/2009 |
| WO | WO 2009/109428 | 9/2009 |

OTHER PUBLICATIONS

U.S. Appl. No. 12/239,136, filed Sep. 26, 2008, Farokhzad, et al.
U.S. Appl. No. 12/301,225, filed Nov. 17, 2008, Farokhzad, et al.
U.S. Appl. No. 12/515,465, filed May 5, 2010, Farokhzad, et al.
U.S. Appl. No. 12/526,300, filed Aug. 11, 2010, Moretti, et al.
Abad, et al., "Comparison of a Monoclonal Antibody-Based Enzyme-Linked Immunosorbent Assay and Gas Chromatography for the Determination of Nicotine in Cigarette Smoke Condensates", *Anal. Chem.*, 65:3227-3231 (1993).
Ackermand & Cresswell, "Cellular mechanisms governing cross-presentation of exogenous antigens", *Nat. Immunol.*, 5(7):678-684 (2004).
Aime, et al., "Lanthanide(III) chelates for NMR biomedical applications", *Chemical Society Reviews*, 27:19-29 (1998).
Akaishi, et al., "Targeting Chemotherapy Using Antibody-Combined Liposome against Human Pancreatic Cancer Cell-Line", *Tohoku J. Exp. Med.*, 175(1):29-42 (1995).
Allen, et al., "Nano-engineering block copolymer aggregates for drug delivery.", *Colloids Surfaces B-Biointerfaces*, 16:3-27 (1999).
Allison, et al., "The mode of action of immunological adjuvants.", *Dev. Biol. Stand.*, 92:3-11 (1998).
Altschul, et al., "Basic local alignment search tool.", *J. Mol Biol.*, 215(3):403-10 (1990).
Altschul, et al., "Gapped BLAST and PSI-BLAST: a new generation of protein database search programs.", *Nucleic Acids Res.*, 25(17):3389-3402 (1997).
Angelucci, et al., "Neuroendocrine transdifferentiation induced by VPA is mediated by PPARD activation and confers resistance to antiblastic therapy in prostate carcinoma", *The Prostate*, 68(6):588-598(2008).
Astete and Sabliov, "Synthesis and characterization of PLGA nanoparticles", *J. Biomat. Sci.,-Polymer Ed.*, 17:247-289 (2006).
Atkinson, et al., "Conjugation of folate via gelonin carbohydrate residues retains ribosomal-inactivating properties of the toxin and permits targeting to folate receptor positive cells.", *J. Biol. Chem.*, 276(30):27930-27935 (2001).
Baba, et al., "Human neutralizing monoclonal antibodies of the IgG1 subtype protect against mucosal simian-human immunodeficiency virus infection.", *Nat. Med.*, 6(2):200-206 (2000).
Babaian, et al., "Radioimmunological imaging of metastatic prostatic cancer with 111indium-labeled monoclonal antibody PAY 276.", *J. Urol.*, 137(3):439-443 (1987).
Bachmann, et al., "T helper cell-independent neutralizing B cell response against vesicular stomatitis virus: role of antigen patterns in B cell induction?", *Eur. J. Immunol.*, 25(12):3445-3451 (1995).
Bagalkot, et al., "An Aptamer-Doxorubicin Physical Conjugate as a Novel Targeted Drug-Delivery Platform", *Angew. Chem. Int. Ed.*, 45(48):8149-8152 (2006).
Bander, et al., "Targeting metastatic prostate cancer with radiolabeled monoclonal antibody J591 to the extracellular domain of prostate specific membrane antigen.", *J. Urol.*, 170(5):1717-1721 (2003).
Barchet, et al., "Virus-induced interferon alpha production by a dendritic cell subset in the absence of feedback signaling in vivo.", *J. Exp. Med.*, 195(4):507-516 (2002).
Barrera, et al., "Synthesis and RGD peptide modification of a new biodegradable copolymer: poly(lactic acid-co-lysine)", *J. Am. Chem. Soc.*, 115(23):11010-11011 (1993).
Bauer, et al., "SMS 201-995: a very potent and selective octapeptide analogue of somatostatin with prolonged action.", *Life Sci.*, 31(11):1133-1140 (1982).
Beaureparie, et al., "Functionalized Fluorescent Oxide Nanoparticles: Artificial Toxins for Sodium Channel Targeting and Imaging at the Single-Molecule Level", *Nano Letters*, 4(11):2079-2083 (2004).
Bennett, et al., "Inhibition of the Aminopeptidase from *Aeromonas Proteolytica* by I-Leucinephosphonic Acid, a Transition State Analogue of Peptide Hydrolysis", *J. Am. Chem. Soc.*, 120(46):12139-12140 (1998).
Binetruy-Tournaire, et al., "Identification of a peptide blocking vascular endothelial growth factor (VEGF)-mediated angiogenesis.", *EMBO J.*, 19(7):1525-1533 (2000).
Bjerke, et al., "Comparison of monoclonal and polyclonal antibodies to continine in nonisotopic and isotopic immunoassays", *J. Immunol. Meth.*, 96:239-246 (1987).
Boes, et al., "T-cell engagement of dendritic cells rapidly rearranges MHC class II transport.", *Nature*, 418(6901):983-988 (2002).
Bonifaz, et al., "Efficient targeting of protein antigen to the dendritic cell receptor DEC-205 in the steady state leads to antigen presentation on major histocompatibility complex class I products and peripheral CD8+ T cell tolerance.", *J. Exp. Med.*, 196(12):1627-1638 (2002).

Bottausci, et al., "Mixing in the shear superposition micromixer: three-dimensional analysis", *Philosophical Transactions of the Royal Society of London Series a-Mathematical Physical and Engineering Sciences*, 362:1001-1018 (2004).

Boussif, et al., "A versatile vector for gene and oligonucleotide transfer into cells in culture and in vivo: polyethylenimine.", *Proc. Natl. Acad. Sci.* USA, 1995, 92:7297-7301 (1995).

Bozzacco, et al., "DEC-205 receptor on dendritic cells mediates presentation of HIV gag protein to CD8+ T cells in a spectrum of human MHC I haplotypes.", *Proc. Nat. Acad. Sci.*, USA, 104(4):1289-1294 (2007).

Brito, et al., "Nanoparticulate carriers for the treatment of coronary restenosis.", *Int J Nanomedicine*, 2(2):143-161 (2007).

Burmeister, et al., "Direct in vitro selection of a 2'-0-methyl aptamer to VEGF.", *Chem Biol*, 12(1):25-33 (2005).

Carino, et al., "Nanosphere based oral insulin delivery,"*J. Control. Release*, 65(1-2):261-9 (2000).

Casola, et al., "B cell receptor signal strength determines B cell fate.", *Nat. Immunol.*, 5(3):317-327 (2004).

Castro & Prieto, "Nicotine Antibody Production: Comparison of two nicotine conjugates in different animal species", *Biochem. Biophys. Res. Comm.*, 67(2):583-589 (1975).

Castro, et al., "Nicotine Antibodies: Comparison of Ligand Specificities of Antibodies Produced against Two Nicotine Conjugates", *Eur. J. Biochem.*, 104:331-340 (1980).

Chacon, et al., "Optimized preparation of poly D,L (lactic-glycolic) microspheres and nanoparticles for oral administration", *Int'l J. Pharmaceutics*, 141:81-91 (1996).

Chaires, et al., "Preferential binding of daunomycin to 5'ATCG and 5'ATCG sequences revealed by footprinting titration experiments.", *Biochemistry*, 29(26):6145-6153 (1990).

Chang, et al., "Five Different Anti-Prostate-specific Membrane Antigen (PSMA) Antibodies Confirm PSMA Expression in Tumor-associated Neovasculature", *Cancer Res.*, 59:3192-3198 (1999).

Cheng, et al., "Formulation of functionalized PLGA-PEG nanoparticles for in vivo targeted drug delivery.", *Biomateriels*, 28(5):869-876 (2007).

Christian, et al., "Nucleolin expressed at the cell surface is a marker of endothelial cells in angiogenic blood vessels.", *J. Cell Biol.*, 163(4):871-878 (2003).

Chu, et al., "Aptamer mediated siRNA delivery", *Nuc. Acid Res.*, 34:e73 (2006).

Chu, et al., "Labeling tumor cells with fluorescent nanocrystal-aptamer bioconjugates.", *Biosens. Bioelectron.*, 21:1859-1866 (2006).

Clark, "The reticulum of lymph nodes in mice studied with the electron microscope.", *Am. J. Anat.*, 110:217-257 (1962).

Connor, et al., "Ex vivo evaluation of anti-EpCAM immunocytokine huKS-IL2 in ovarian cancer.", *J. Immunother.*, 27(3):211-219 (2004).

Croy and Kwon, "Polymeric micells for drug delivery", *Curr. Pharm. Design*, 12:4669-4684 (2006).

D'Antonio, et al., "Longitudinal analysis of androgen deprivation of prostate cancer cells identifies pathways to androgen independence", *The Prostate*, 68(7):698-714 (2008).

Dang and Rock, "Stimulation of B lymphocytes through surface Ig receptors induces LFA-1 and ICAM-1-dependent adhesion.", *J. Immunol.*, 146(10):3273-3279 (1991).

De Graaf, et al., "A fully human anti-Ep-CAM scFv-beta-glucuronidase fusion protein for selective chemotherapy with a glucuronide prodrug.", *Br. J. Cancer*, 86(5):811-818 (2002).

De Jaeghere, et al., "Freeze-drying and lyopreservation of diblock and triblock poly(lactic acid)-poly(ethylene oxide) (PLA-PEO) copolymer nanoparticles.", *Pharm. Dev. Technol.*, 5(4)473-483 (2000).

Delemarre, et al., "Repopulation of macrophages in popliteal lymph nodes of mice after liposome-mediated depletion.", *J. Leukoc. Biol.*, 47(3):251-257 (1990).

Demello and Demello, "Microscale reactors: nanoscale products.", *Lab on a Chip*, 4(2):11N-15N (2004).

Demello, "Control and detection of chemical reactions in microfluidic systems.", *Nature*, 442(7101):394-402 (2006).

Deming, et al., "Facile synthesis of block copolypeptides of defined architecture.", *Nature*, 390(6658):386-389 (1997).

Derfus, et al., "Intracellular Delivery of Quantum Dots for Live Cell Labeling and Organelle Tracking", *Advanced Materials*, 16:961-966 (2004).

Dimarco and Arcamone, "DNA complexing antibiotics: Daunomycin, adriamycin and their derivates.", *Arzneim-Forsch. (Drug Res.)*, 25:368-375 (1975).

Ding, et al., "Syntheses of conformationally constricted molecules as potential NAALADase/PSMA inhibitors.", *Org. Lett.*, 6(11):1805-1808 (2004).

Dinkla, et al., "Identification of a streptococcal octapeptide motif involved in acute rheumatic fever.",*J. Biol Chem.*, 282(26):18686-18693 (2007).

Dykxhoorn, et al., "Killing the messenger: short RNAs that silence gene expression.", *Nat. Rev. Mol. Cell Biol.*, 4(6):457-467 (2003).

Eklund, et al., "Denileukin diftitox: a concise clinical review.", *Expert Rev. Anticancer Ther.*, 5(1):33-38 (2005).

Elbashir, et al., "RNA interference is mediated by 21- and 22-nucleotide RNAs.", *Genes Dev.*, 15(2):188-200 (2001).

Eldridge, et al., "Biodegradable microspheres as a vaccine delivery system," *Mol. Immunol.*, 28(3):287-94 (1991).

Elsässer-Beile, et al., "A new generation of monoclonal and recombinant antibodies against cell-adherent prostate specific membrane antigen for diagnostic and therapeutic targeting of prostate cancer.", *Prostate*, 66(13):1359-1370 (2006).

Farokhazad, et al., "Nanoparticle-Aptamer Bioconjugates: A New Approach for Targeting Prostate Cancer Cells," *Cancer Research*, 64:7668-7672 (2004).

Farokhzad, et al., "Nanoparticle—aptamer bioconjugates for cancer targeting", *Expert Opin. Drug Delivery*, 3(3):311-324 (2006).

Farokhzad, et al., "Targeted nanoparticle-aptamer bioconjugates for cancer chemotherapy in vivo.", *Proc. Natl. Acad. Sci.*, USA, 103(16):6315-6320 (2006).

Farr, et al., "The structure of the sinus wall of the lymph node relative to its endocytic properties and transmural cell passage.",*Am. J. Anat.*, 157(3):265-284 (1980).

Fire, et al., "Potent and specific genetic interference by double-stranded RNA in *Caenorhabditis elegans.*", *Nature*, 391(6669):806-811 (1998).

Fonseca, et al., "Paclitaxel-loaded PLGA nanoparticles: preparation, physicochemical characterization and in vitro anti-tumoral activity.", *J. Control. Release*, 83(2):273-286 (2002).

Fracasso, et al., "Anti-tumor effects of toxins targeted to the prostate specific membrane antigen.", *Prostate*, 53(1):9-23 (2002).

Francis, et al., "A phase I trial of antibody directed enzyme prodrug therapy (ADEPT) in patients with advanced colorectal carcinoma or other CEA producing tumours.", *Br. J. Cancer*, 87(6):600-607 (2002).

Frankel, et al., "Phase I trial of a novel diphtheria toxin/granulocyte macrophage colony-stimulating factor fusion protein (DT388GMCSF) for refractory or relapsed acute myeloid leukemia. ", *Clin Cancer Res.*, 8(5):1004-1013 (2002).

Frederick, et al., "Structural comparison of anticancer drug-DNA complexes: adriamycin and daunomycin.", *Biochemistry*, 29(10):2538-2549 (1990).

Froidevaux, et al., "Somatostatin analogs and radiopeptides in cancer therapy.", *Biopolymers*, 66(3):161-183 (2002).

Fujita, et al., "Cytokine profiling of prostatic fluid from cancerous prostate glands identifies cytokines associated with extent of tumor and inflammation", *The Prostate*, 68(8):872-882 (2008).

Gao, et al., "A method for the generation of combinatorial antibody libraries using pIX phage display," *Proc. Natl. Acad. Sci. U.S.A.*, 99(20): 12612-6 (2002).

Gao, et al., "In vivo cancer targeting and imaging with semiconductor quantum dots.", *Nat. Biotechnol.*, 22(8):969-976 (2004).

Gao, et al., "In vivo molecular and cellular imaging with quantum dots.", *Curr. Op. Biotechnol.*, 16:63-72 (2005).

Gershlick, "Treating atherosclerosis: local drug delivery from laboratory studies to clinical trials," *Atherosclerosis*, 160(2): 259-71 (2002).

Billies, et al., "An anti-CD20-IL-2 immunocytokine is highly efficacious in a SCID mouse model of established human B lymphoma.", *Blood*, 105(10):3972-3978 (2005).

Grauer, et al., "Identification, purification, and subcellular localization of prostate-specific membrane antigen PSM' protein in the LNCaP prostatic carcinoma cell line.", *Cancer Res.*, 58(21):4787-4789 (1998).

Gref, et al., "Biodegradable long-circulating polymeric nanospheres.", *Science*, 263(5153):1600-1603 (1994).

Haensler, et al., "Polyamidoamine cascade polymers mediate efficient transfection of cells in culture", *Bioconjugate Chem.*, 4(5):372-379 (1993).

Haj, et al., "New findings in the study on the intercalation of bisdaunorubicin and its monomeric analogues with naked and nucleus DNA.", *Chem. Biol. Interact.*, 145(3):349-358 (2003).

Hanes, et al., "Polymer microspheres for vaccine delivery.", *Pharm. Biotechnol.*, 6:389-412 (1995).

Hangartner, et al, "Antiviral immune responses in gene-targeted mice expressing the immunoglobulin heavy chain of virus-neutralizing antibodies.", *Proc. Natl. Acad. Sci.*, USA, 100:12883-12888 (2003).

Hannon, et al., "Unlocking the potential of the human genome with RNA interference", *Nature*, 431(7006):371-378 (2004).

Harada and Kataoka, "Supramolecular assemblies of block copolymers in aqueous media as nanocontainers relevant to biological applications", *Progress Polymer Sci.*, 31(11):949-982 (2006).

Harper, et al., "Efficacy of a bivalent L1 virus-like particle vaccine in prevention of infection with human papillomavirus types 16 and 18 in young women: a randomised controlled trial.", *Lancet*, 364(9447):1757-1765 (2004).

Haseloff and Gerlach, "Simple RNA enzymes with new and highly specific endoribonuclease activities.", *Nature*, 334(6183):585-591 (1988).

Hawiger, et al., "Dendritic cells induce peripheral T cell unresponsiveness under steady state conditions in vivo.", *J. Exp. Med.* 194(1):769-779 (2001).

He, et al., "A microRNA polycistron as a potential human oncogene," *Nature*, 435(7043): 828-833 (2005).

Hélène, "The anti-gene strategy: control of gene expression by triplex-forming-oligonucleotides.", *Anticancer Drug Des.* 6(6):569-584 (1991).

Helene, et al., "Control of gene expression by triple helix-forming oligonucleotides. The antigene strategy.", *Ann, N.Y. Acad. Sci.* 660:27-36 (1992).

Hermann and Patel, "Adaptive recognition by nucleic acid aptamers," *Science*, 287: 820-825 (2000).

Hieda, et al., "Active Immunization Alters the Plasma Nicotine Concentration in Rats", *J. Pharmacol. Exp. Therapeutics*, 283:1076-1081 (1997).

Hieda, et al., "Immunization of rats reduces nicotine distribution to brain", *Psychopharmacology*, 143:150-157 (1999).

Horoszewicz, et al., "Monoclonal antibodies to a new antigenic marker in epithelial prostatic cells and serum of prostatic cancer patients.", *Anticancer Res.*, 7(5B):927-935 (1987).

Houghton, "General method for the rapid solid-phase synthesis of large numbers of peptides: Specificity of antigen-antibody interaction at the level of individual amino acids", *Immunol.*, 82:5131-5135 (1985).

Jackson, et al., "Design and pharmacological activity of phosphinic acid based NAALADase inhibitors.", *J. Med. Chem.*, 44(24):4170-4175 (2001).

Jackson, et al., "Design of NAALADase inhibitors: a novel neuroprotective strategy.", *Curr. Med. Chem.*, 8(8):949-957 (2001).

Johnson and Prud'Homme, "Mechanism for rapid self-assembly of block copolymer nanoparticles.", *Phys. Rev. Lett.*, 91(11):118302 (2003).

Jones and Leroux, "Polymeric micelles—a new generation of colloidal drug carriers", *Eur. J. Pharmaceutics Biopharmaceutics*, 48:101-111 (1999).

Jung, et al., "Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice", *Pharmaceutical Research*, 18(3):352-360 (2001).

Junt, et al., "Subcapsular sinus macrophages in lymph nodes clear lymph-borne viruses and present them to antiviral B cells", *Nature*, 450:110-116 (2007).

Kabanov, et al., "DNA Complexes with Polycations for the Delivery of Genetic Material into Cells", *Bioconjugate Chem.*, 6(1):7-20 (1995).

Kamentsky, "Laser scanning cytometry.", *Methods Cell Biol.*, 63:51-87 (2001).

Kanashiro, et al., "Inhibition of mutant p53 expression and growth of DMS-153 small cell lung carcinoma by antagonists of growth hormone-releasing hormone and bombesin.", *Proc. Natl. Acad. Sci.*, USA, 100(26):15836-15841 (2003).

Karlin and Altschul, "Applications and statistics for multiple high-scoring segments in molecular sequences.", *Proc. Natl Acad. Sci. USA*, 90(12):5873-5877 (1993).

Karlin and Altschul, "Methods for assessing the statistical significance of molecular sequence features by using general scoring schemes.", *Proc. Nat Acad Sci. USA*, 87:2264-2268 (1990).

Karrer, et al., "On the key role of secondary lymphoid organs in antiviral immune responses studied in alymphoplastic (aly/aly) and spleenless (Hox11(-)/-) mutant mice.", *J. Exp. Med.*, 185(12):2157-2170 (1997).

Kelly, et al., "The Optical Properties of Metal Nanoparticles: The Influence of Size, Shape, and Dielectric Environment", *J. Phys. Chem. B.*, 107(3):668-677 (2003).

Khademhosseini, et al., "Cell docking inside microwells within reversibly sealed microfluidic channels for fabricating multiphenotype cell arrays," *Lab Chip*, 5(12):1380-6 (2005).

Knight, et al., "Hydrodynamic Focusing on a Silicon Chip: Mixing Nanoliters in Microseconds", *Phys. Rev. Lett.*, 80:3863-3866 (1998).

Köhrer and Rajbhandary, "Proteins carrying one or more unnatural amino acids," In Ibba, et al., (ads.), *Aminoacyl-tRNA Synthetases*, Landes Bioscience, Chapter 31 (2005).

Köhrer, et al, "Complete set of orthogonal 21st aminoacyl-tRNA synthetase-amber, ochre and opal suppressor tRNA pairs: concomitant suppression of three different termination codons in an mRNA in mammalian cells.", *Nucleic Acids Res.*, 32(21):6200-6211 (2004).

Köhrer, et al., "Import of amber and ochre suppressor tRNAs into mammalian cells: a general approach to site-specific insertion of amino acid analogues into proteins.", *Proc. Natl. Acad. Sci.*, USA, 98(25):14310-14315 (2001).

Koivunen, et al., "Phage libraries displaying cyclic peptides with different ring sizes: ligand specificities of the RGD-directed integrins.", *Biotechnology* (NY), 13(3):265-270 (1995).

Koivunen, et al., "Tumor targeting with a selective gelatinase inhibitor", *Nat. Biotechnol.*, 17:768-774 (1999).

Konan, et al., "Preparation and characterization of sterile sub-200 nm meso-tetra(4-hydroxylphenyl)porphyrin-loaded nanoparticles for photodynamic therapy", *Eur. J. Pharmaceutics Biopharmaceutics*, 55:115-124 (2003).

Kozikowski, et al., "Synthesis of urea-based inhibitors as active site probes of glutamate carboxypeptidase II: efficacy as analgesic agents.", *J. Med. Chem.*, 47(7):1729-1738 (2004).

Krieg, et al., "CpG motifs in bacterial DNA trigger direct B-cell activation.", *Nature*, 374(6522):546-549 (1995).

Kreitman, et al., "Efficacy of the anti-CD22 recombinant immunotoxin BL22 in chemotherapy-resistant hairy-cell leukemia.", *N. Engl J. Med.*, 345(4):241-347 (2001).

Kreitman, et al., "Phase I trial of recombinant immunotoxin anti-Tac(Fv)-PE38 (LMB-2) in patients with hematologic malignancies.", *J. Clin. Oncol.*, 18(8):1622-1636 (2000).

Kukowska-Latallo, et al., "Efficient transfer of genetic material into mammalian cells using Starburst polyamidoamine dendrimers", *Proc. Natl. Acad. Sci.*, USA, 93(10):4897-4902 (1996).

Kumar, et al., "Inhibition of angiogenesis and tumor growth by SCH221153, a dual alpha(v)beta3 and alpha(v)beta5 integrin receptor antagonist.", *Cancer Res.*, 61(5):2232-2238 (2001).

Kwon, et al., "Pseudopoly(amino acids): A study of the synthesis and characterization of poly(acyl-hydroxyproline-esters)", *Macromolecules*, 22:3250-3255 (1989).

Laakkonen, et al., "Antitumor activity of a homing peptide that targets tumor lymphatics and tumor cells.", *Proc. Natl. Acad. Sci.*, USA, 101(25):9381-9386 (2004).

Labhasetwar, et al., "Arterial uptake of biodegradable nanoparticles: Effect of surface modifications ,"*J. Pharm. Sci.*, 87(10): 1229-34 (1998).

Langer, "Biomaterials in drug delivery and tissue engineering: one laboratory's experience.", *Acc. Chem. Res.*, 33(2):94-101 (2000).

Langer, "New methods of drug delivery," *Science*, 249(4976):1527-33 (1990).

Langer, "Selected advances in drug delivery and tissue engineering", *J. Control. Release*, 62:7-11 (1999).

Langone, et al., "Nicotine and its metabolites. Radioimmunoassays for nicotine and cotinine", *Biochem.*, 12(24):5025-5030 (1973).

Langone & Van Vunakis, "Radioimmunoassay of Nicotine, Cotinine, and 0-(3-Pyridyl)-0-oxo-N-methylbutyramide", *Met. Enzymol.*, 84:628-640 (1982).

Leamon, et al., "Cytotoxicity of folate-*Pseudomonas* exotoxin conjugates toward tumor cells. Contribution of translocation domain.", *J. Biol. Chem.*, 268(33):24847-24854 (1993).

Leamon, et al., "Selective targeting of malignant cells with cytotoxin-folate conjugates."*J. Drug Target.*, 2(2):101-112 (1994).

Leopold, et al., "Fluorescent virions: dynamic tracking of the pathway of adenoviral gene transfer vectors in living cells.", *Human Gene Therapy*, 9(3):367-378 (1998).

Leroy, et al., "Radioimmunodetection of lymph node invasion in prostatic cancer. The use of iodine 123 (123I)-labeled monoclonal anti-prostatic acid phosphatase (PAP) 227 A F(ab')2 antibody fragments in vivo.", *Cancer*, 64(1):1-5 (1989).

Leucuta, et al., "Albumin microspheres as a drug delivery system for epirubicin: pharmaceutical, pharmacokinetic and biological aspects," *International Journal of Pharmaceutics*, 41: 213-7 (1988).

Lim, et al., "A Self-Destroying Polycationic Polymer: Biodegradable Poly(4-hydroxy-I-proline ester)", *J. Am. Chem. Soc.*, 121(24):5633-5639 (1999).

Lim, et al., "Cationic hyperbranched poly(amino ester): a novel class of DNA condensing molecule with cationic surface, biodegradable three-dimensional structure, and tertiary amine groups in the interior.", *J. Am. Chem. Soc*, 123(10):2460-2461 (2001).

Lin, et al., "A microRNA polycistron as a potential human oncogene p828", *Nature*, 435(7043):828-833(2005).

Lin, et al., "Well-Ordered Mesoporous Silica Nanoparticles as Cell Markers", *Chem. Mater.*, 17:4570-4573 (2005).

Liu, et al., "Cell-Surface labeling and internalization by a fluorescent inhibitor of prostate-specific membrane antigen", *The Prostate*, 68(9):955-964 (2008).

Liu, et al, "Constitutive and antibody-induced internalization of prostate-specific membrane antigen.", *Cancer Res.*, 58(18):4055-4060 (1998).

Liu, et al., "Folate-targeted enzyme prodrug cancer therapy utilizing penicillin-V amidase and a doxorubicin prodrug.", *J. Drug Target.*, 7:43-53 (1999).

Liu, et al., "Hypermethylation of MCAM gene is associated with advanced tumor stage in prostate cancer", *The Prostate*, 68(4):418-426 (2008).

Liu, et al., "Monoclonal antibodies to the extracellular domain of prostate-specific membrane antigen also react with tumor vascular endothelium.", *Cancer Res.*, 57(17):3629-3634 (1997).

Low, et al., "Folate receptor-targeted drugs for cancer and inflammatory diseases.", *Adv. Drug Deliv. Rev.*, 56(8):1055-1058 (2004).

Lu, et al., "MicroRNA expression profiles classify human cancers", *Nature*, 435(7043):834-838 (2005).

Ludewig, et al., Induction of optimal anti-viral neutralizing B cell responses by dendritic cells requires transport and release of virus particles in secondary lymphoid organs, *Eur. J. Immunol.*, 30(1):185-196 (2000).

Lupold, et al., "Identification and characterization of nuclease-stabilized RNA molecules that bind human prostate cancer cells via the prostate-specific membrane antigen.", *Cancer Res.*, 62(14):4029-4033 (2002).

Lyu, et al., "The immunocytokine scFv23/TNF sensitizes HER-2/neu-overexpressing SKBR-3 cells to tumor necrosis factor (TNF) via up-regulation of TNF receptor-1.", *Mol. Cancer Ther.*, 4(8):1205-1213 (2005).

Maher, "DNA triple-helix formation: An approach to artificial gene repressors?", *Bioassays* 14:807-815 (1992).

Majer, et al., "Synthesis and biological evaluation of thiol-based inhibitors of glutamate carboxypeptidase II: discovery of an orally active GCP II inhibitor.", *J. Med. Chem.*, 46(10):1989-1996 (2003).

Manolova, et al., "Nanoparticles target distinct dendritic cell populations according to their size", *Eur. J. Immunol.*, 38:1404-1413 (2008).

Manz, et al., "Capillary electrophoresis on a chip", *J. Chromatography*, 593:253-258 (1992).

Mathiowitz, et al., "Polyanhydride Microspheres as Drug Carriers I. Hot Melt Encapsulation"*J. Control. Release*, 5:13-22 (1987).

Mathiowitz, et al., "Novel microcapsules for delivery systems", *Reactive Polymers*, 6:275-283 (1987).

Mathiowitz, et al., "Polyanhydride Microspheres as Drug Carriers. II.Microencapsulation by Solvent Removal", *J. Appl. Polymer Sci.*, 35:755-774 (1988).

Mattheakis, et al., "Optical coding of mammalian cells using semiconductor quantum dots.", *Analytical Biochemistry*, 327(2):200-208 (2004).

Maung, et al., "Probing for a hydrophobic a binding register in prostate-specific membrane antigen with phenylalkylphosphonamidates.", *Bioorg. Med. Chem.*, 12(18):4969-4979 (2004).

McDevitt, et al., "An alpha-particle emitting antibody ([213Bi]J591) for radioimmunotherapy of prostate cancer.", *Cancer Res.*, 60(21):6095-6100 (2000).

McDevitt, et al., "Tumor therapy with targeted atomic nanogenerators.", *Science*, 294(5546):1537-1540 (2001).

Mead, et al., "Laboratory vector competence of black flies (Diptera:Simuliidae) for the Indiana serotype of vesicular stomatitis virus.", *Ann. N.Y. Acad. Sci.*, 916:437-443 (2000).

Meister, et al., "Mechanisms of gene silencing by double-stranded RNA.", *Nature*, 431(7006):343-349 (2004).

Melani, et al., "Targeting of interleukin 2 to human ovarian carcinoma by fusion with a single-chain Fv of antifolate receptor antibody.", *Cancer Res.*, 58(18):4146-4154 (1998).

Mempel, et al., "T-cell priming by dendritic cells in lymph nodes occurs in three distinct phases.", *Nature*, 427(6970):154-159 (2004).

Metelitsa, et al., "Antidisialoganglioside lgranulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis.", *Blood*, 99(11):4166-4173 (2002).

Meyers, et al., "Development of monoclonal antibody imaging of metastatic prostatic carcinoma.", *Prostate*, 14(31:209-220 (1989).

Milligan and Uhlenbeck, "Synthesis of small RNAs using T7 RNA polymerase," *Methods in Enzymology*, 180: 51-62 (1989).

Moghimi, et al., "Long-circulating and target-specific nanoparticles: theory to practice," *Pharmacal. Rev.*, 53(2): 283-318 (2001).

Mulligan, "The basic science of gene therapy," *Science*, 260(5110):926-32 (1993).

Murphy, et al., "Isolation and characterization of monoclonal antibodies specific for the extracellular domain of prostate specific membrane antigen.", *J. Urol.*, 160(6 Pt 2):2396-2401 (1998).

Murray, et al., "Synthesis and characterization of monodisperse nanocrystals and close-packed nanocrystal assemblies", *Ann. Rev. Mat. Sci.*, 30:545-610 (2000).

Myers and Miller, *CABIOS* (1988).

Nan, et al., "Dual function glutamate-related ligands: discovery of a novel, potent inhibitor of glutamate carboxypeptidase II possessing mGluR3 agonist activity.", *J. Med. Chem.*, 43(5):772-774 (2000).

Neidle, "The molecular basis for the action of some DNA-binding drugs.", *Prog. Med. Chem.*, 16:151-221 (1979).

Nguyen and Wu, "Micromixers—a review.", *J. Micromechan. Microeng.*, 15:R1 (2005).

Notter, et al., "Targeting of a B7-1 (CD80) immunoglobulin G fusion protein to acute myeloid leukemia blasts increases their costimulatory activity for autologous remission T cells.", *Blood*, 97(10):3138-3145 (2001).

Ochsenbein, et al., "Protective T cell-independent antiviral antibody responses are dependent on complement.", *J. Exp. Med.*, 190(8):1165-1174 (1999).

Ochsenbein, et al., "Control of early viral and bacterial distribution and disease by natural antibodies.", *Science*, 286(5447):2156-2159 (1999).

O'Donnell, et al., "c-Myc-regulated microRNAs modulate E2F1 expression," *Nature*, 435(7043): 839-843 (2005).

Okada, et al., "Antigen-engaged B cells undergo chemotaids toward the T zone and form motile conjugates with helper T cells.", *PLoS Biol.*, 3(6):e150 (2005).

Oliver, et al., "Conformational and SAR analysis of NAALADase and PSMA inhibitors.", *Bioorg. Med. Chem.*, 11(20):4455-4461 (2003).

Pape, et al., "The humoral immune response is initiated in lymph nodes by B cells that acquire soluble antigen directly in the follicles.", *Immunity*, 26(4):491-502 (2007).

Papisov, "Acyclic Polyacetals from Polysaccharides: Biomimetic Biomedical "Stealth" Polymers", *ACS Symposium Series*, 786:301-314 (2001).

Parekh, et al., "Biomarkers for Prostate Cancer Detection", *The Journal of Urology*, 178(6):2252-2259 (2007).

Pasqualini, et al., "Aminopeptidase N is a receptor for tumor-homing peptides and a target for inhibiting angiogenesis.", *Cancer Res.*, 60(3):722-727 (2000).

Patri, et al., "Synthesis and in Vitro Testing of J591 Antibody—Dendrimer Conjugates for Targeted Prostate Cancer Therapy", *Bioconj. Chem.*, 15:1174-1181 (2004).

Pellegrino, et al., "On the development of colloidal nanoparticles towards multifunctional structures and their possible use for biological applications.", *Small*, 1(1):48-63 (2005).

Pfohl, et al., "Trends in microfluidics with complex fluids.", *Chemphyschem*, 4(12):1291-1298 (2003).

Phillips, et al., "Enhanced antibody response to liposome-associated protein antigens: preferential stimulation of IgG2a/b production.", *Vaccine*, 10(3):151-158 (1992).

Porkka, et al., "A fragment of the HMGN2 protein homes to the nuclei of tumor cells and tumor endothelial cells in vivo.", *Proc. Natl. Acad. Sci.*, USA, 99(11):7444-7449 (2002).

Putnam, et al., "Poly(4-hydroxy-l-proline ester): Low-Temperature Polycondensation and Plasmid DNA Complexation", *Macromolecules*, 32(11):3658-3662 (1999).

Qi, et al., "Extrafollicular activation of lymph node B cells by antigen-bearing dendritic cells", *Science*, 312(5780):1672-1676 (2006).

Quintanar-Guerrero, et al., "Preparation Techniques and Mechanisms of Formation of Biodegradable Nanoparticles from Preformed Polymers", *Drug Dev. Industrial Pharmacy*, 24(12):1113-1128 (1998).

Reddy, et al., "Exploiting lymphatic transport and complement activation in nanoparticle vaccines", *Nat. Biotech.*, 25(10):1159-1164 (2007).

Reif, et al., "Balanced responsiveness to chemoattractants from adjacent zones determines B-cell position.", *Nature*, 416(6876):94-99 (2002).

Reiher, et al., "Inhibition of tumor growth by systemic treatment with thrombospondin-1 peptide mimetics.", *Int. J. Cancer*, 98(5):682-689 (2002).

Reubi, et al., "Peptide receptors as molecular targets for cancer diagnosis and therapy.", *Endocr. Rev.*, 24(4):389-427 (2003).

Reynolds, et al., "Rational siRNA design for RNA interference.", *Nat. Biotechnol.*, 22(3):326-330 (2004).

Robbins, et al., "Stable expression of shRNAs in human CD34+ progenitor cells can avoid induction of interferon responses to siRNAs in vitro", *Nature Biotechnology*, 24(5):566-571 (2006).

Robinson, et al., "LEAPT: lectin-directed enzyme-activated prodrug therapy.", *Proc. Natl. Acad. Sci.*, USA, 101(40):14527-14532 (2004).

Roost, et al., "Mapping of the dominant neutralizing antigenic site of a virus using infected cells.", *J. Immunol. Methods*, 189(2):233-242 (1996).

Rossbacher and Shlomchik, "The B cell receptor itself can activate complement to provide the complement receptor 1/2 ligand required to enhance B cell immune responses in vivo.", *J. Exp. Med.*, 198(4):591-602 (2003).

Sampson, et al., "Progress report of a Phase I study of the intracerebral microinfusion of a recombinant chimeric protein composed of transforming growth factor (TGF)-alpha and a mutated form of the *Pseudomonas* exotoxin termed PE-38 (TP-38) for the treatment of malignant brain tumors.", *J. Neurooncol.*, 65(1):27-35 (2003).

Santoyo, et al., "Highly specific and accurate selection of siRNAs for high-throughput functional assays.", *Bioinformatics*, 21(8):1376-1382 (2005).

Sarver, et al., "Ribozymes as potential anti-HIV-1 therapeutic agents.", *Science* 247(4947):1222-1225 (1990).

Schally, et al., "Peptide analogs in the therapy of prostate cancer.", *Prostate*, 45(2):158-166 (2000).

Schultz, "Plasmon resonant particles for biological detection", *Curr. Op. Biotechnol.*, 14:13-22 (2003).

Schultz, et al., "Single-target molecule detection with nonbleaching multicolor optical immunolabels.", *Proc. Natl. Acad. Sci.*, USA, 97(3):996-1001(2000).

Shaida, et al., "Expression of BNIP3 correlates with hypoxia-inducible factor (HIF)-10, HIF-20 and the androgen receptor in prostate cancer and is regulated directly by hypoxia but not androgens in cell lines", *The Prostate*, 68(3):336-343 (2008).

Shen, et al., "Enhanced and prolonged cross-presentation following endosomal escape of exogenous antigens encapsulated in biodegradable nanoparticles", *Immunol.*, 117:78-88 (2006).

Shestopalov, et al., "Multi-step synthesis of nanoparticles performed on millisecond time scale in a microfluidic droplet-based system.", *Lab on a Chip*, 4(4):316-321 (2004).

Shiow, et al., "CD69 acts downstream of interferon-alpha/beta to inhibit S1P1 and lymphocyte egress from lymphoid organs.", *Nature*, 440(7083):540-544 (2006).

Silver, et al., "Prostate-specific membrane antigen expression in normal and malignant human tissues.", *Clin. Cancer Res.*, 3(1):81-85 (1997).

Smith-Jones, et al., "In vitro characterization of radiolabeled monoclonal antibodies specific for the extracellular domain of prostate-specific membrane antigen.", *Cancer Res.*, 60(18):5237-5243 (2000).

Sondel, et al., "Preclinical and clinical development of immunocytokines.", *Curr. Opin. Investig. Drugs*, 4(6):696-700 (2003).

Song, et al., "A Microfluidic System for Controlling Reaction Networks in Time", *Angewandte Chemie-Int'l Ed.*, 42:768-772 (2003).

Spooner, et al., "A novel vascular endothelial growth factor-directed therapy that selectively activates cytotoxic prodrugs.", *Br. J. Cancer*, 88(10):1622-1630 (2003).

Stoermer, et al., "Synthesis and biological evaluation of hydroxamate-Based inhibitors of glutamate carboxypeptidase II.", *Bioorg. Med. Chem. Lett.*, 13(13):2097-2100 (2003).

Storm, et al., "Surface Modification of Nanoparticles to Oppose Uptake by the Mononuclear Phagocyte System", *Adv. Drug Deliv. Rev.*, 17:31-48 (1995).

Stroock, et al., "Chaotic mixer for microchannels.", *Science*, 295(5555):647-651 (2002).

Sutcliffe, et al., "Antibodies that react with predetermined sites on proteins", *Science*, 219:660-666 (1983).

Tang, et al., "In Vitro Gene Delivery by Degraded Polyamidoamine Dendrimers", *Bioconjugate Chem.*, 7:703-714 (1996).

Tang, et al., "Prostate targeting ligands based on N-acetylated alpha-linked acidic dipeptidase.", *Biochem. Biophys. Res. Commun.*, 307(1):8-14 (2003).

Taylor, et al., "Macrophage receptors and immune recognition.", *Annu. Rev. Immunol.*, 23:901-944 (2005).

Tindall, et al., "The Rationale for Inhibiting 50-Reductase Isoenzymes in the Prevention and Treatment of Prostate Cancer", *The Journal of Urology*, 179(4):1235-1242 (2008).

Trindade, et al., "Nanocrystalline Semiconductors: Synthesis, Properties, and Perspectives", *Chem. Mat.*, 13(11):3843-3858 (2001).

Tsukamoto, et al., "Phosphonate and phosphinate analogues of N-acylated gamma-glutamylglutamate. potent inhibitors of glutamate carboxypeptidase II.", *Bioorg. Med. Chem. Lett.*, 12(16):2189-2192 (2002).

Uhrich, et al., "Polymeric Systems for Controlled Drug Release", *Chem. Rev.*, 99(11):3181-3198 (1999).

Unkeless, et al., "Structure and function of human and murine receptors for IgG.", *Annu. Rev. Immunol.*, 6:251-281 (1998).

Uwatoku, et al., "Application of Nanoparticle Technology for the Prevention of Restenosis After Balloon Injury in Rats," *Circ. Res.*, 92(7): e62-9 (2003).

Valentini, et al., "Association of anthracycline derivatives with DNA: a fluorescence study.", *Farmaco [Sci]*, 40:377-390 (1985).

Vallabhajosula, et al., "Radioimmunotherapy of prostate cancer in human xenografts using monoclonal antibodies specific to prostate specific membrane antigen (PSMA): studies in nude mice.", *Prostate*, 58(2):145-155 (2004).

Vascotto, et al., "Antigen presentation by B lymphocytes: how receptor signaling directs membrane trafficking.", *Curr., Opin., Immunol.*, 19(1):93-98 (2007).

Vihko, et al., "Radioimaging of Prostatic Carcinoma With Prostatic Acid Phosphatase—Specific Antibodies", *Biotechnology in Diagnostics*, 131-134 (1985).

Von Allmen, et al., "V domain of RAGE interacts with AGEs on prostate carcinoma cells", *The Prostate*, 68(7):748-758 (2008).

Von Andrian and Mempel, "Homing and cellular traffic in lymph nodes.", *Nat. Rev. Immunol.*, 3(11):867-878 (2003).

Wang, et al., "A novel biodegradable gene carrier based on polyphosphoester.", *J. Am. Chem. Soc.*, 123(38):948-9481 (2001).

Wang, et al., "Autoantibody signatures in prostate cancer.", *N Engl J Med*, 353(12):1224-1235 (2005).

Wang, et al., "Identification of prostate specific membrane antigen (PSMA) as the target of monoclonal antibody 107-1A4 by proteinchip; array, surface-enhanced laser desorption/ionization (SELDI) technology.", *Int J. Cancer*, 92(6):871-876 (2001).

Wang, et al., "Interactions between an anthracycline antibiotic and DNA: molecular structure of daunomycin complexed to d(CpGpTpApCpG) at 1.2-A resolution.", *Biochemistry*, 26(4):1152-1163 (1987).

Weaver, et al., "Transferrin receptor ligand-targeted toxin conjugate (Tf-CRM107) for therapy of malignant gliomas.", *J. Neurooncol.*, 65(1):3-13 (2003).

Wessels, et al., "Studies of group B streptococcal infection in mice deficient in complement component C3 or C4 demonstrate an essential role for complement in both innate and acquired immunity.",*Proc. Natl. Acad. Sci.*, USA, 92(25):11490-11494 (1995).

Whelan, et al., "Efficient recovery of infectious vesicular stomatitis virus entirely from cDNA clones.", *Proc. Natl. Acad. Sci.*, USA, 92(18):8388-8392 (1995).

Wilson, et al., "The Structure of an Antigenic Determinant in a Protein", *Cell*, 37:767-778 (1984).

Wind, et al., "An integrated confocal and magnetic resonance microscope for cellular research.", *J. Magn. Reson.*, 147(2):371-377 (2000).

Wlotzka, et al., "In vivo properties of an anti-GnRH Spiegelmer: an example of an oligonucleotide-based therapeutic substance class," *Proc. Natl. Acad. Sci. U. S. A.*, 99(13):8898-8902 (20021.

Wright, et al., "Cyclophosphamide/granulocyte colony-stimulating factor causes selective mobilization of bone marrow hematopoietic stem cells into the blood after M phase of the cell cycle.", *Blood*, 97(8):2278-2285 (2001).

Wu, "Arming antibodies: prospects and challenges for immunoconjugates.", *Nat. Biotechnol.*, 23(9):1137-1146 (2005).

Wu, et al., "Immunofluorescent labeling of cancer marker Her2 and other cellular targets with semiconductor quantum dots.", *Nat. Biotechnol.*, 21(1):41-46 (2003).

Yang, "Imaging of vascular gene therapy.", *Radiology*, 228:36-249 (2003).

Yoo, et al., "In vitro and in vivo anti-tumor activities of nanoparticles based on doxorubicin-PLGA conjugates.", *J. Control. Release*, 68(3):419-431 (2000).

Yuan, et al., "siRNA Selection Server: an automated siRNA oligonucleotide prediction server.", *Nucl. Acids. Res.*, 32:W130-W134 (2004).

Zamore, et al., "RNAi: double-stranded RNA directs the ATP-dependent cleavage of mRNA at 21 to 23 nucleotide intervals.", *Cell*, 101(1):25-33 (2000).

Zauner, et al., "Polylysine-basedtransfection systems utilizing receptor-mediated delivery.", *Adv. Drug Del. Rev.*, 30:97-113 (1998).

Zhang, et al., "The proliferative effect of estradiol on human prostate stromal cells is mediated through activation of ERK", *The Prostate*, 68(5):508-516 (2008).

Zheng, et al., "Highly fluorescent, water-soluble, size-tunable gold quantum dots.", *Phys. Rev. Lett.*, 93(7):077402 (2004).

Zhou, et al., "Investigation on a novel core-coated microspheres protein delivery system.", *J. Control. Release*, 75(1-2):27-36 (2001).

Zhou, et al., "Preparation of poly(L-serine ester): a structural analog of conventional poly(L-serine)", *Macromolecules*, 23(14):3399-3406 (1990).

Zuker, "Mfold web server for nucleic acid folding and hybridization prediction", *Nuc. Acid. Res.*, 31:3406-3415 (2003).

Bies et al., Lectin-medicated drug targeting: history and applications, *Advanced Drug Delivery Reviews*, 56:425-435 (2004).

Bocca, et al., "Phagocytic uptake of fluorescent slealth solid lipid nanoparticles", *Int. J. Pharmaceutics*, 175:185-193 (1998).

Brooking et al., "Transport of Nanoparticles Across the Rat Nasal Mucosa", *Journal of Drug Targeting*, 9(4):267-279 (2001).

Chandy et al., "Development of Poly(Lactic Acid)/Chitosan Co-Matrix Microspheres: Controlled Release of Taxol-Heparin for Preventing Restenosis", *Drug Delivery*, 8:77-86 (2001).

Chandy, et al, "5-Fluorouracil-loaded chitosan coated polylactic acid pmicrospheres as biodegradable drug carriers for cerebral tumors", *J. Microencapsulation*, 17(5):625-638 (2000).

Cheng, et al., "Formulation of functionalized PLGA-PEG nanoparticles for in vivo targeted drug delivery", *Biomaterrials*, 28:869-875 (2007).

Coppi, et al, "Chitosan-Alginate Microparticles as a Protein Carrier", *Drug Development and Industrial Pharmacy*, 27(5):393-400 (2001).

Elvassore, et al., "Production iof Insulin-Loaded Poly(Ethylene Glycol)/Poly(*I*-Lactide) (PEG/PLA) Nanoparticles by Gas Antisolvent Techniques", *Journal of Pharmacrutical Sciences*, 90(10):1628-36 (2001).

Ermak and Giannasca, "Microparticle targeting to M cells", *Advanced Drug Delivery Reviews*, 34:261-283 (1998).

Fi Li Povic-Grcic et al., "Mucoadhesive chitosan-coated liposomes: characteristics and stability", *J. Microencapsulation*, 18 1:3-12 (2001).

Gaserod et al., "The enhancement of the bioadhesive properties of calcium alginate gel beads by coating with chitosan", *Intl. J. of Pharmaceutics*, 175:237-246 (1998).

Hejaz et al., "Stomach-specific anti-H. pylon therapy. I: preparation and characterization of tetracyline-loaded chitosan microshpheres", *Intl. J. of Pharmaceutics*, 235:87-94 (2002).

Huang et al., "Microencapsulation of Chlorpheniramine Maleate-Resin Particles with Crosslinked Chitosan for Sustained Release", *Pharmaceutical Development and Technology*, 4 1:107-115 (1999).

Janes et al., "Chitosan nanoparticles as delivery systems for doxorubicin", *Journal of Controlled Release*, 73:255-267 (2001).

Jayasena, "Aptamers: An Emerging Class of Molecules That Rival Antibodies in Diagnostics", *Clinical Chemistry*, 45(9):1628-1650 (1999).

Kawashima, et al., "Mucoadhesive DL-Lactide/Glycolide Copolymer Nanoshperes Coated with Chitosan to Improve Oral Delivery of Elcatonin", *Pharmaceutical Development and Technology*, 5(1):77-85 (2000).

Khandare, et al., "Polymer-drug conjugates: Progress in polymeric prodrugs," *Progress in Polymer Science*, 31(4): 359-397 (2006).

Kim, et al., "Target-specific cellular uptake of PLGA nanoparticles coated with poly(L-lysine)-poly(ethyleneglycol)-folate conjugate", *Langmuir*, 21(19): 8852-8857 (2005).

Lehr, "Lectin-mediated drug delivery: The second generation of bioadhesives", *J. of Controlled Release*, 65:19-29 (2000).

Lim et al., "Preparation and evaluation of the in vitro drug release properties and mucoadhesion of novel microspheres of hyaluronic acid and chitosan", *J. of Controlled Release*, 66:281-292 (2000).

Mi, et al., "Release of Indomethacin from a Novel Chitosan Microsphere Prepared by a Natrually Occurring Crosslinker: Examination of Crosslinking and Polycation-Anionic Drug Interaction", *J. of Applied Polymer Science*, 81:1700-1711 (2001).

Olivier, et al., "Drug Transport to Brain with Targeted Nanoparticles", *J. of the Am. Society of Experimental Neuro Therapeutics*, 2:108-119 (2005).

Pimentel, et al., "Peptide nanoparticles as novel immunogens: design and analysis of a prototypic severe acute respiratory syndrome vaccine", *Chemical Biology & Drug Design*, 73(1):53-61 (2009).

Ponchel, et al., "Specific and non-specific bioadhesive particulate systems for oral delivery to the gastrointestinal tract", *Advanced Drug Delivery Reviews*, 34:191-219 (1998).

Shimoda, et al., "Bloadhesive Characteristics of Chitosan Mircroshperes to the Mucosa of Rat Small Intestine", *Drug Delvelopment and Inustrial Pharmacy*, 27(6):567-576 (2001).

Simberg, et al., "Biomimetic amplification of nanoparticle homing to tumors", *Nat'l Acad. Sic. USA*, 104(3):921-936 (2007).

Takeuchi, et al., "Enteral Absorption of Insulin in Rats from Mucoadhesive Chitosan-Coated Liposomes", *Pharmaceutical Research*, 13(6):896-901 (1996).

Takeuchi, et al., "Spray-Dried Lactose Composite Particles Containing an Ion Complex of Alginate-Chitosan for Desinging a Dry-Coated Tablet Having a Time-Controlled Releasing Function", *Pharmaceutical Research*, 17 (1):94-99 (2000).

Takeuchi et al., "Mucoashesive Lipsomes Coated with Chitosan or Carbopol for Oral Administration of Peptide Drugs", *Proceed. Intl. Symp. Control. Rel. Mont. Mater.*, 26:988-989 (1999).

Tavitian, et al., "In vivo imaging with oligonucleotides for diagnosis and drug development", *Gut, 52 Su*, I IV :40-47 (2003).

Tobio, et al "Role of PEG on the stability in digestive fluids and in vivo fate of PEG-PLA nanoparticles following oral administration", *Colloids and Surfaces B: Biointerferences*, 18:315-323 (2000).

Vila, et al., "Design of biodegradable particles for protein delivery", *Journal of Controlled Release*, 78:15-24 (2002).

Vila, et al., "PLA-PEG Nanospheres: New Carriers for Transmucosal Delivery of Proteins and Plasmid DNA", *Poly. Adv. Technol.*, 13:851-858 (2002).

Yamada, et al., "In Vitro and in Vivo Evaluation of Sustained Release Chitosan-Coat Ketoprofen Microparticles", *Yakugaku Zasshi*, 121(3):239-245 (2001).

Yourong, et al, "Preparation of DHAQ-loaded mPEG-PLGA-mPEG nanoparticles and evaluation of drug release behaviors in vitro/in vivo," *J. Mat. Sci.: Mat. Med.*, 17(6): 509-16 (2006).

Yuan, et al., "Intranasal immunization with chitosan/pCETP nanoparticles inhibits atherosclerosis in a rabbit model of atherosclerosis", *Vaccine, Bittetwortit Scientific*, 26:29-30 (2008).

Heald, et al., "Poly(lactic acid)-poly(ethylene oxide) (PLA-PEG) nanoparticles: NMR studies of the central solidlike PLA core and the liquid PEG corona", *Langmuir*, 18;3689-3675 (2002).

Tomal et al., "Resiquimod and other immune response modifiers as vaccine adjuvants", Expert Rev Vaccines, 6:835-847 (2007) Abstract Only.

Villa, et al., "PLA-PEG particles as nasal protein carriers: the influence of the particle size", *Int. J Pharmaceut.*, 292:43-52 (2005).

International Search Report mailed Jun. 27, 2008.

Cerchia, et al. "Neutralizing aptamrrs from whole-cell SELEX inhibit the RET receptor tyrosine kinase", PLoS Biology, 3(4):849-60 (2005).

Foss, et al., "Radiolabeled small-molecule ligands for prostate-specific membrane antigen: in vivo imaging in experimental models of prostate cancer" , Clin. Cancer Res., 11:4022-28 (2005).

Govender, et al., "Defining the drug incorporation properties of PLA-PEG nanoparticles" , Intl J of Pharmaceutics, 1999:95-110(2000).

Mitra, et al., "Tumour targeted delivery of encapsulated dextran-doxorubicin conjugate using chitosan nanoparticles as carrier" , J Controlled Release, 74:317-23 (2001).

Wu, et al., ng-circulation Poly(ethylene glycol)-poly(D,L-lactide) block copolymermicelles with modulated surace chane, J Contl Rel., 77:27-38 (2001).

Zhou, et al., "NAAG peptidase inhibitors and their potential for diagnosis and therapy" , Nature Rev. Drug Disc., 4:1015-26 (2005).

\* cited by examiner

POLYMER-ENCAPSULATED REVERSE MICELLES

RELATED APPLICATIONS

This application is a continuation of Application No. PCT/US2008/059483 filed Apr. 4, 2008, which claims priority to U.S. Provisional Application No. 60/910,062, filed Apr. 4, 2007, titled "Reverse Micelle Nanoprecipitation: A Method for Encapsulating Nucleic Acids in Biodegradable Polymers," which is incorporated herein by reference in its entirety. Additionally, the contents of any patents, patent applications, and references cited throughout this specification are hereby incorporated by reference in its entirety.

STATEMENT REGARDING FEDERALLY SPONSORED RESEARCH OR DEVELOPMENT

This invention was made with government support under grant number U54 CA119349 awarded by the National Institutes of Health. The government has certain rights in the invention.

FIELD OF INVENTION

The present invention generally relates to pharmaceutical compositions comprising reverse micelle particles useful in the treatment of diseases.

BACKGROUND

The delivery of a drug to a patient with controlled-release of the active ingredient has been an active area of research for decades and has been fueled by the many recent developments in polymer science. In addition, controlled release polymer systems can be designed to provide a drug level in the optimum range over a longer period of time than other drug delivery methods, thus increasing the efficacy of the drug and minimizing problems with patient compliance.

Biodegradable particles have been developed as sustained release vehicles used in the administration of small molecule drugs, proteins, peptide drugs, and nucleic acids. The drugs are typically encapsulated in a polymer matrix which is biodegradable and biocompatible. As the polymer is degraded and/or as the drug diffuses out of the polymer, the drug is released into the body.

Currently, many methods exist for forming nanoparticles of biodegradable polymers. However, due to the slow partitioning of hydrophilic molecules into the hydrophobic nanoparticle core, methods of encapsulating charged hydrophilic agents, such as nucleic acids, have been plagued by low encapsulation yield, low drug-to-carrier weight ratios, irreproducibility, and often require emulsification at high shear rates to achieve nanoparticle size, resulting in product losses.

Thus, there is a need for a method of incorporating hydrophilic therapeutic agents into nanoparticles.

SUMMARY OF THE INVENTION

The present invention provides a method for efficiently encapsulating therapeutic agents, e.g., nucleic acids of potential therapeutic or diagnostic interest, in biodegradable polymers using a nanoprecipitation method by first forming non-toxic reverse micelles. These reverse micelles effectively entrap therapeutic agents, such as hydrophilic therapeutic agents, and disperse them into a nanosuspension, facilitating their incorporation into the hydrophobic core of biodegradable polymers. This technique improves: encapsulation yield, drug-to-carrier weight ratio, and reproducibility of nanoparticle formation, without requiring the use of potentially damaging emulsification techniques. Further, the methods of the disclosed invention use components, or segments of components, that are naturally-derived or FDA-approved for use in humans, thereby generating clinically relevant drug delivery vehicles.

As such, the present invention is directed toward a pharmaceutical composition, comprising a plurality of target-specific stealth nanoparticles comprising a reverse micelle, a polymeric matrix, a targeting moiety, and a therapeutic agent. In one embodiment, the nanoparticle has an amount of targeting moiety effective for the treatment of cancer in a subject in need thereof. In another embodiment, the targeting moiety is an aptamer.

In one embodiment, the polymeric matrix of the reverse micelle nanoparticle comprises two or more polymers, such as polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, or combinations thereof. In one embodiment, the polymeric matrix comprises one or more polyesters, polyanhydrides, polyethers, polyurethanes, polymethacrylates, polyacrylates or polycyanoacrylates. In a particular embodiment, the polymeric matrix comprises a polyalkylene glycol, such as polyethylene glycol. In another embodiment, the polymeric matrix comprises PLGA, PLA, PGA, or a polycaprolactone. In still another embodiment, the polymeric matrix comprises a copolymer of two or more polymers, such as a copolymer of PLGA or PLA and PEG. The polymeric matrix can comprise PLGA or PLA and a copolymer of PLGA or PLA and PEG.

In another embodiment, the polymeric matrix comprises a lipid-terminated polyalkylene glycol and a polyester, such as a lipid-terminated PEG and PLGA. As described below, the lipid can be of the Formula V, such as 1,2 distearoyl-sn-glycero-3-phosphoethanolamine (DSPE), and salts thereof.

In one embodiment of the reverse micelle nanoparticle of the invention, a portion of the polymer matrix is covalently bound to the targeting moiety, such as via the free terminus of PEG, or via a carboxyl group at the free terminus of PEG, or via a maleimide functional group at the free terminus of PEG.

In one embodiment, the reverse micelle nanoparticle of the invention has a ratio of ligand-bound polymer to non-functionalized polymer effective for the treatment of cancer.

The therapeutic agent can be encapsulated within the reverse micelle of the nanoparticle. The therapeutic agent can be a nucleic acid, such as natural or unnatural siRNAs, shRNAs, microRNAs, ribozymes, DNA plasmids, aptamers, antisense oligonucleotides, randomized oligonucleotides, or ribozymes. In a particular embodiment, the therapeutic agent is an siRNA, such as an siRNA molecule that is complementary to tumor-related targets, such as an anti-PLK1 siRNA or an anti-VEGF siRNA.

In one embodiment of the nanoparticle of the invention, the reverse micelle comprises an amphipathic lipid, such as lecithin, phosphatidylcholine, lipid A, cholesterol, dolichol, shingosine, sphingomyelin, ceramide, cerebroside, sulfatide, glycosylceramide, phytosphingosine, phosphatidylethanolamine, phosphatidylglycerol, phosphatidylinositol, phosphatidylserine, cardiolipin, phophatidic acid, and lysophophatides. In one embodiment, the therapeutic agent is a nucleic acid, and the ratio of amphipathic lipid to nucleic acid is approximately 33:1.

In another aspect, the invention provides a method of treating prostate cancer in a subject in need thereof, comprising administering to the subject an effective amount of the pharmaceutical composition of the invention. The pharmaceutical composition can be administered directly to the prostate of a subject or directly to prostate cancer cells, such as administered directly to prostate cancer cells by injection into tissue comprising the prostate cancer cells. In another embodiment, the pharmaceutical composition is administered to the subject by implantation of nanoparticles at or near prostate cancer cells during surgical removal of a tumor. The pharmaceutical composition can be administered systemically, such as intravenously.

The pharmaceutical composition of the invention can be used in the manufacture of a medicament for the treatment of cancer, such as prostate cancer. The pharmaceutical composition can be administered intravenously.

In another embodiment, the nanoparticle has an amount of targeting moiety effective for the treatment of a cancer wherein PSMA is expressed on the surface of cancer cells or in the tumor neovasculature in a subject in need thereof. The PSMA-related indication can be selected from the group consisting of prostate cancer, non-small cell lung cancer, colorectal carcinoma, and glioblastoma.

In another aspect, the invention provides a nanoparticle comprising a reverse micelle, wherein the reverse micelle is encapsulated by a polymer, and a therapeutic agent, wherein the therapeutic agent is a nucleic acid.

In another aspect, the invention provides a particle for drug delivery comprising a hydrophilic agent entrapped in a reverse micelle, wherein the interior of the reverse micelle is hydrophilic and the exterior is hydrophobic, and wherein the reverse micelle is encapsulated by a polymer. The hydrophilic agent can be a nucleic acid, such as a DNA, an RNA, an siRNA, shRNA, microRNA, aptamer, plasmid, chromosome, ribozymes, or antisense oligonucleotide, a protein, a small molecule, or a charged agent.

The reverse micelle of the particle of the invention can comprise an amphipathic lipid, such as lecithin, DPAP, phosphatidylcholine, lipid A, cholesterol, dolichol, shingosine, sphingomyelin, ceramide, cerebroside, sulfatide, glycosylceramide, phytosphingosine, phosphatidylethanolamine, phosphatidylglycerol, phosphatidylinositol, phosphatidylserine, cardiolipin, phophatidic acid, and lysophophatides. In one embodiment, the amphipathic lipid is neutral. In another embodiment, the amphipathic lipid is cationic.

In another embodiment of the particle, the polymer is poly (lactic acid), poly(glycolic acid), poly(lactic-co-glycolic acid), poly(caprolactone), or poly (anhydride). The overall charge on the particle can be negative or neutral.

Furthermore, the particle of the invention can be combined with a pharmaceutically acceptable excipient to form a pharmaceutical composition.

In another aspect, the invention provides a method of preparing a particle of the invention, the method comprising steps of: providing a therapeutic agent; dissolving the therapeutic agent with an amphipathic lipid in a volatile, water-miscible organic solvent; forming reverse micelles, wherein the interior of the reverse micelle is hydrophilic and contains the therapeutic agent, and the exterior of the reverse micelle is hydrophobic; adding a polymer to the mixture of reverse micelles; combining the resulting mixture with a hydrophilic non-solvent that the polymer is not soluble in to form nanoparticle by rapid diffusion of the solvent into the non-solvent, and evaporation of the solvent. The therapeutic agent used in the method can be a hydrophilic agent, such as a nucleic acid. The solvent can be tetrahydrofuran, acetone, acetonitrile, or dimethylformamide. The non-solvent is water, ethanol, methanol, or mixtures thereof. The polymer of the method comprises a copolymer of two or more polymers, such as a copolymer of PLGA and PEG, or PLA and PEG.

In one embodiment, the nanoparticles of the invention is less than 100 nm in diameter.

DETAILED DESCRIPTION OF THE INVENTION

Figure 1:
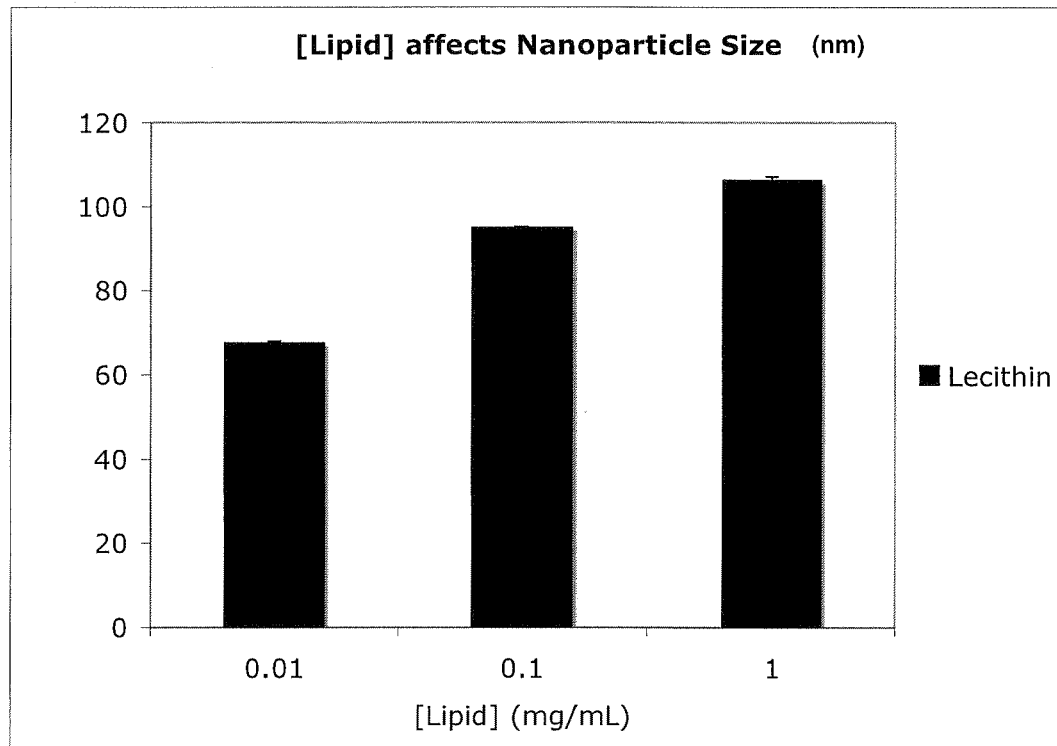
FIG. 1 demonstrates the effect of amphipathic lipid concentration on encapsulation particle size.

The present invention generally relates to particles, and, in particular, polymer-encapsulated reverse micelles. One aspect of the invention is directed to a method of developing polymer-encapsulated reverse micelles with desired properties, wherein the micelles contain a targeting moiety (also referred to as a "ligand"), such as an aptamer. One or more of the polymers may be a biocompatible polymer (e.g., homopolymer, copolymer or block copolymer), wherein the biocompatible polymer may be conjugated to a targeting moiety such as an aptamer. In some cases, the polymer-encapsulated reverse micelles may contain a therapeutic agent, e.g., a drug.

In one embodiment, the polymer-encapsulated reverse micelle of the invention has an amount of targeting moiety (e.g., an aptamer) effective for the treatment of a disease, e.g., prostate cancer, in a subject in need thereof. In certain embodiments, the targeting moiety is conjugated to a polymer. Thus, in one embodiment, the polymer-encapsulated reverse micelle comprises a polymer that is functionalized with a targeting moiety. In other embodiments, the polymer-encapsulated reverse micelle comprises a certain ratio of targeting moiety-conjugated polymer to non-functionalized polymer. The reverse micelle can have an optimized ratio of these two polymers, such that an effective amount of ligand is associated with the reverse micelle for treatment of a disease, e.g., prostate cancer. For example, increased ligand density (e.g., on a PLGA-PEG copolymer) will increase target binding (cell binding/target uptake), making the reverse micelle "target specific." Alternatively, a certain concentration of non-functionalized polymer (e.g., non-functionalized PLGA-PEG copolymer) in the reverse micelle can control inflammation and/or immunogenicity (i.e., the ability to provoke an immune response), and allow the reverse micelle to have a circulation half-life that is adequate for the treatment of cancer (e.g., prostate cancer). Furthermore, the non-functionalized polymer can lower the rate of clearance from the circulatory system via the reticuloendothelial system. Thus, the non-functionalized polymer gives the reverse micelle "stealth" characteristics. In a particular embodiment, the stealth polymer is PEG. Additionally, the non-functionalized polymer balances an otherwise high concentration of ligands, which can otherwise accelerate clearance by the subject, resulting in less delivery to the target cells.

By having targeting moieties, the "target specific" reverse micelles are able to efficiently bind to or otherwise associate with a biological entity, for example, a membrane component or cell surface receptor. Targeting of a therapeutic agent (e.g., to a particular tissue or cell type, to a specific diseased tissue but not to normal tissue, etc.) is desirable for the treatment of tissue specific diseases such as cancer (e.g. prostate cancer). For example, in contrast to systemic delivery of a cytotoxic anti-cancer agent, targeted delivery could prevent the agent from killing healthy cells. Additionally, targeted delivery can allow for the administration of a lower dose of the agent, which could reduce the undesirable side effects commonly associated with traditional chemotherapy. As discussed herein, the target specificity of the reverse micelle of the invention will be maximized by optimizing the ligand density on the reverse micelle.

Polymer-Encapsulated Reverse Micelles

For the purposes of the invention, the term "reverse micelle" referees to a micelle in which a hydrophilic component is in the inner portion of the micelle. A typical micelle in aqueous solution forms an aggregate with the hydrophilic head regions in contact with surrounding solution, sequestering the hydrophobic tail regions in the micelle center. Thus, the hydrophilic portion of the polymer-encapsulated reverse micelle, which is on the inner portion of the reverse micelle, can effectively entrap therapeutic agents, including hydrophilic therapeutic agents such as nucleic acids.

The reverse micelle of the present invention comprises an amphipathic lipid. As used herein, the term "amphipathic" refers to a property where a molecule has both a polar portion and a non-polar portion. Often, an amphipathic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the invention, the amphipathic compound can be, but is not limited to, one or a plurality of the following: naturally derived lipids, surfactants, or synthesized compounds with both hydrophilic and hydrophobic moieties.

Specific examples of amphipathic compounds include, but are not limited to, lecithin, phosphatidylcholine, lipid A, cholesterol, dolichol, shingosine, sphingomyelin, ceramide, cerebroside, sulfatide, glycosylceramide, phytosphingosine, phosphatidylethanolamine, phosphatidylglycerol, phosphatidylinositol, phosphatidylserine, cardiolipin, phophatidic acid, and lysophophatides.

In one embodiment, the amphipathic lipid is dimethyldiotadecylammonium bromide (DDAB).

In a particular embodiment, an amphipathic component that can be used to form the reverse micelle is lecithin, and, in particular, phosphatidylcholine. Lecithin is an amphiphilic lipid and, as such, forms a phospholipid bilayer having the hydrophilic (polar) heads facing their surroundings, which are oftentimes aqueous, and the hydrophobic tails facing each other. Lecithin has an advantage of being a natural lipid that is available from, e.g., soybean, and already has FDA approval for use in other delivery devices. In addition, a mixture of lipids such as lethicin is more advantageous than one single pure lipid.

In certain embodiments of the invention, the amphiphilic layer of the nanoparticle, e.g., the layer of lecithin, is a monolayer, meaning the layer is not a phospholipid bilayer, but exists as a single continuous or discontinuous layer around, or within, the nanoparticle. The amphiphilic layer is "associated with" the nanoparticle of the invention, meaning it is positioned in some proximity to the polymeric matrix, such as surrounding the outside of the polymeric shell, or dispersed within the polymers that make up the nanoparticle.

In one embodiment, the ratio of amphipathic lipid to nucleic acid is approximately 50:1, 40:1, 30:1, 20:1, and 10:1, molar. In a particular embodiment, the ratio of amphipathic lipid to nucleic acid is approximately 33:1, molar.

In some embodiments, a therapeutic agent and/or targeting moiety (e.g., an aptamer) can be associated with the polymer-encapsulated reverse micelle. In some embodiments, the targeting moiety can be covalently associated with the surface of the polymer that encapsulates the reverse micelle. In some embodiments, covalent association is mediated by a linker. In some embodiments, the therapeutic agent can be encapsulated within the reverse micelle.

Thus, in one embodiment, the invention provides a polymer-encapsulated reverse micelle comprising 1) PLGA; 2) PEG; 3) an amphipathic lipid (e.g., lecithin); and 4) a covalently attached targeting moiety. In one embodiment, the PLGA and PEG are copolymers, and the targeting moiety is covalently bound to PEG. In another embodiment, the PEG is bound to DSPE, which self assembles with PLGA, and the low molecular weight PSMA ligand is covalently bound to PEG.

In another embodiment, the invention comprises a polymer-encapsulated reverse micelle comprising 1) a polymeric matrix comprising a biodegradable polymer; 2) an amphipathic lipid; 3) a stealth polymer, and 4) a covalently attached targeting moiety. In another embodiment, the invention comprises a polymer-encapsulated reverse micelle comprising 1) a polymeric matrix comprising a biodegradable polymer; 2) lecithin; 3) a stealth polymer, and 4) a covalently attached targeting moiety.

Any polymer may be used in accordance with the present invention. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

A "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer is biologically derived, i.e., a biopolymer. Non-limiting examples of polymers include peptides or proteins (i.e., polymers of various amino acids), or nucleic acids such as DNA or RNA. In some cases, additional moieties may also be present in the polymer, for example biological moieties such as those described below.

If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

It should be understood that, although the terms "first," "second," etc. may be used herein to describe various elements, including polymeric components, these terms should not be construed as being limiting (e.g., describing a particular order or number of elements), but rather, as being merely descriptive, i.e., labels that distinguish one element from another, as is commonly used within the field of patent law. Thus, for example, although one embodiment of the invention may be described as having a "first" element present and a "second" element present, other embodiments of the invention may have a "first" element present but no "second" element present, a "second" element present but no "first" element present, two (or more) "first" elements present, and/or two (or more) "second" elements present, etc., and/or additional elements such as a "first" element, a "second" element, and a "third" element, without departing from the scope of the present invention.

Various embodiments of the present invention are directed to copolymers, which, in particular embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer is a first block of the block copolymer and the second polymer is a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers.

For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) is amphiphilic, i.e., having a hydrophilic portion and a hydrophobic portion, or a relatively hydrophilic portion and a relatively hydrophobic portion. A hydrophilic polymer is one generally that attracts water and a hydrophobic polymer is one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about) 60°. In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) of the present invention includes a biocompatible polymer, i.e., the polymer that does not typically induce an adverse response when inserted or injected into a living subject, for example, without significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject. One simple test to determine biocompatibility is to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly(glycerol sebacate), polyglycolide, polylactide, PLGA, polycaprolactone, or copolymers or derivatives including these and/or other polymers.

In certain embodiments, the biocompatible polymer is biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly (lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene inline), PEGylated poly(ethylene imine), poly(L-lactide-co-L-lysine), poly(serine ester), poly (4-hydroxy-L-proline ester), poly[a-(4-aminobutyl)-L-glycolic acid], and derivatives thereof.

In some embodiments, the polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In particular embodiments, by optimizing the ratio of lactic acid to glycolic acid monomers in the polymer of the reverse micelle (e.g., the PLGA block copolymer or PLGA-PEG block copolymer), reverse micelle parameters such as water uptake, therapeutic agent release (e.g., "controlled release") and polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine) (Zauner et al., 1998, *Adv. Drug Del. Rev.*, 30:97; and Kabanov et al., 1995, *Bioconjugate Chem.*, 6:7), poly(ethylene imine) (PEI; Boussif et al, 1995, *Proc. Natl. Acad. Sci., USA*, 1995, 92:7297), and poly(amidoamine) dendrimers (Kukowska-Latallo et al., 1996, *Proc. Natl. Acad. Sci., USA*, 93:4897; Tang et al., 1996, *Bioconjugate Chem.*, 7:703; and Haensler et al., 1993, *Bioconjugate Chem.*, 4:372) are positively-charged at physiological pH, form ion pairs with nucleic acids, and mediate transfection in a variety of cell lines.

In some embodiments, polymers can be degradable polyesters bearing cationic side chains (Putnam et al., 1999, *Macromolecules*, 32:3658; Barrera et al., 1993, *J. Am. Chem. Soc.*, 115:11010; Urn et al., 1999, *J. Am. Chem. Soc.*, 121:5633; and Zhou et al, 1990, *Macromolecules*, 23:3399). Examples of these polyesters include poly(L-lactide-co-L-lysine) (Barrera et al, 1993, *J. Am. Chem. Soc.*, 115:11010), poly(serine ester) (Zhou et al, 1990, *Macromolecules*, 23:3399), poly(4-hydroxy-L-proline ester) (Putnam et al, 1999, *Macromolecules*, 32:3658; and Lim et al., 1999, *J. Am. Chem. Soc.*, 121:5633). Poly(4-hydroxy-L-proline ester) was demonstrated to condense plasmid DNA through electrostatic interactions, and to mediate gene transfer (Putnam et al., 1999, *Macromolecules*, 32:3658; and Lim et al., 1999, *J. Am. Chem. Soc.*, 121:5633). These new polymers are less toxic than poly(lysine) and PEI, and they degrade into non-toxic metabolites.

A polymer (e.g., copolymer, e.g., block copolymer) containing poly(ethylene glycol) repeat units is also referred to as a "PEGylated" polymer. Such polymers can control inflammation and/or immunogenicity (i.e., the ability to provoke an immune response) and/or lower the rate of clearance from the circulatory system via the reticuloendothelial system, due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. In some cases, the addition of poly (ethylene glycol) repeat units may increase plasma half-life of the polymer (e.g., copolymer, e.g., block copolymer), for instance, by decreasing the uptake of the polymer by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS(N-hydroxysuccinimide) to react a polymer to a PEG group terminating in an amine, by ring opening polymerization techniques (ROMP), or the like.

In addition, certain embodiments of the invention are directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer, such as a hydrolyzable polymer, containing carboxylic acid groups, may be conjugated with poly(ethylene glycol) repeat units to form a poly(ester-ether).

In a particular embodiment, the molecular weight of the polymers of the reverse micelles of the invention are optimized for effective treatment of cancer, e.g., prostate cancer. For example, the molecular weight of the polymer influences reverse micelle particle degradation rate (particularly when the molecular weight of a biodegradable polymer is adjusted), solubility, water uptake, and drug release kinetics (e.g. "controlled release"). As a further example, the molecular weight of the polymer can be adjusted such that the reverse micelle biodegrades in the subject being treated within a reasonable period of time (ranging from a few hours to 1-2 weeks, 3-4 weeks, 5-6 weeks, 7-8 weeks, etc.). In particular embodiments of a reverse micelle comprising a copolymer of PEG and PLGA, the PEG has a molecular weight of 1,000-20,000, e.g., 5,000-20,000, e.g., 10,000-20,000, and the PLGA has a molecular weight of 5,000-100,000, e.g., 20,000-70,000, e.g., 20,000-50,000.

In certain embodiments, the polymers of the reverse micelles may be conjugated to a lipid. The polymer may be, for example, a lipid-terminated PEG. As described below, the lipid portion of the polymer can be used for self assembly with another polymer, facilitating the formation of a reverse micelle. For example, a hydrophilic polymer could be conjugated to a lipid that will self assemble with a hydrophobic polymer.

In some embodiments, lipids are oils. In general, any oil known in the art can be conjugated to the polymers used in the invention. In some embodiments, an oil may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In a particular embodiment, the lipid is of the Formula V:

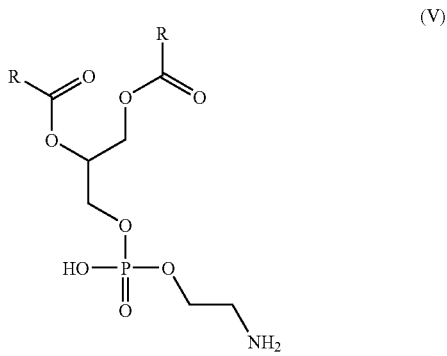

and salts thereof, wherein each R is, independently, $C_{1-30}$ alkyl. In one embodiment of Formula V, the lipid is 1,2 distearoyl-sn-glycero-3-phosphoethanolamine (DSPE), and salts thereof, e.g., the sodium salt.

The properties of the polymers discussed herein, and methods for preparing them, are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al, 2001, *J. Am. Chem. Soc.*, 123:9480; Lim et al., 2001, *J. Am. Chem. Soc.*, 123:2460; Langer, 2000, *Ace. Chem. Res.*, 33:94; Langer, 1999, *J. Control. Release*, 62:7; and Uhrich et al., 1999, *Chem. Rev.*, 99:3181). More generally, a variety of methods for synthesizing suitable polymers are described in *Concise Encyclopedia of Polymer Science and Polymeric Amines and Ammonium Salts*, Ed. by Goethals, Pergamon Press, 1980; *Principles of Polymerization* by Odian, John Wiley & Sons, Fourth Edition, 2004; *Contemporary Polymer Chemistry* by Allcock et al., Prentice-Hall, 1981; Deming et al, 1997, *Nature*, 390:386; and in U.S. Pat. Nos. 6,506,577, 6,632,922, 6,686,446, and 6,818,732.

In still another set of embodiments, a particle (comprising, e.g., a copolymer, e.g., a block copolymer) of the present invention includes a therapeutic agent, i.e., an agent that has a therapeutic or prophylactic effect when given to a subject. Examples of therapeutic moieties to be used with the reverse micelles of the present invention include therapeutic nucleic acids, antineoplastic or cytostattc agents or other agents with anticancer properties, or a combination thereof.

In some cases, the polymer-encapsulated reverse micelle has a characteristic dimension of less than about 1 micrometer. For example, the particle may have a characteristic dimension of the particle may be less than about 300 nm, less than about 200 nm, less than about 150 nm, less than about 100 nm, less than about 50 nm, less than about 30 nm, less than about 10 nm, less than about 3 nm, or less than about 1 nm in some cases. In particular embodiments, the nanoparticle of the present invention has a diameter of less than 100 nm.

Yet another aspect of the invention is directed to reverse micelles having more than one polymer present, and libraries involving such reverse micelles. For example, in one set of embodiments, reverse micelles may contain more than one distinguishable polymers (e.g., copolymers, e.g., block copolymers), and the ratios of the two (or more) polymers may be independently controlled, which allows for the control of properties of the particle. For instance, a first polymer may be a polymeric conjugate comprising a targeting moiety and a biocompatible portion, and a second polymer may comprise a biocompatible portion but not contain the targeting moiety. Control of the amounts of these polymers within the reverse micelle may thus be used to control various physical, biological, or chemical properties of the reverse micelle, for instance, the size of the reverse micelle (e.g., by varying the molecular weights of one or both polymers), the surface charge (e.g., by controlling the ratios of the polymers if the polymers have different charges or terminal groups), the surface hydrophilicity (e.g., if the polymers have different molecular weights and/or hydrophilicities), the surface density of the targeting moiety (e.g., by controlling the ratios of the two or more polymers), etc.

As a specific example, a reverse micelle may comprise a first polymer comprising a poly(ethylene glycol) and a targeting moiety conjugated to the poly(ethylene glycol), and a second polymer comprising the poly(ethylene glycol) but not the targeting moiety, or comprising both the poly(ethylene glycol) and the targeting moiety, where the poly(ethylene glycol) of the second polymer has a different length (or number of repeat units) than the poly(ethylene glycol) of the first polymer. As another example, a reverse micelle may comprise a first polymer comprising a first biocompatible portion and a targeting moiety, and a second polymer comprising a second biocompatible portion different from the first biocompatible portion (e.g., having a different composition, a substantially different number of repeat units, etc.) and the targeting moiety. As yet another example, a first polymer may comprise a biocompatible portion and a first targeting moiety, and a second polymer may comprise a biocompatible portion and a second targeting moiety different from the first targeting moiety.

Targeting Moieties

In yet another set of embodiments a reverse micelle of the present invention includes a targeting moiety, i.e., a moiety able to bind to or otherwise associate with a biological entity, for example, a membrane component, a cell surface receptor, prostate specific membrane antigen, or the like. For example, a targeting portion may cause the particles to become localized to a tumor, a disease site, a tissue, an organ, a type of cell, etc. within the body of a subject, depending on the targeting moiety used. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

The targeting moiety (e.g., an aptamer) can be covalently bonded the polymeric matrix component of the reverse micelle. In some embodiments, the targeting moiety can be covalently associated with the surface of the polymeric component (e.g., PEG). In some embodiments, covalent association is mediated by a linker. In some embodiments, the therapeutic agent can be associated with the surface of, encapsulated within, surrounded by, and/or dispersed throughout the polymeric matrix.

A targeting moiety may be a nucleic acid, polypeptide, glycoprotein, carbohydrate, or lipid. For example, a targeting moiety can be a nucleic acid targeting moiety (e.g. an aptamer) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g., a growth factor, hormone, LDL, transferrin, etc. A targeting moiety can be an antibody, which term is intended to include antibody fragments, characteristic portions of antibodies, single chain targeting moieties can be identified, e.g., using procedures such as phage display. This widely used technique has been used to identify cell specific ligands for a variety of different cell types.

In some embodiments, targeting moieties bind to an organ, tissue, cell, extracellular matrix component, and/or intracellular compartment that is associated with a specific developmental stage or a specific disease state. In some embodiments, a target is an antigen on the surface of a cell, such as a cell surface receptor, an integrin, a transmembrane protein, an ion channel, and/or a membrane transport protein. In some embodiments, a target is an intracellular protein. In some embodiments, a target is a soluble protein, such as immunoglobulin. In certain specific embodiments, a target is a tumor marker. In some embodiments, a tumor marker is an antigen that is present in a tumor that is not present in normal tissue. In some embodiments, a tumor marker is an antigen that is more prevalent in a tumor than in normal tissue. In some embodiments, a tumor marker is an antigen that is more prevalent in malignant cancer cells than in normal cells.

In some embodiments, a target is preferentially expressed in tumor tissues versus normal tissues. For example, when compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al., 1997, *Clin. Cancer Res.*, 3:81).

In some embodiments, inventive targeted reverse micelles comprise less than 50% by weight, less than 40% by weight, less than 30% by weight, less than 20% by weight, less than 15% by weight, less than 10% by weight, less than 5% by weight, less than 1% by weight, or less than 0.5% by weight of the targeting moiety.

In some embodiments, the targeting moieties are covalently associated with the reverse micelle. In some embodiments, covalent association is mediated by a linker.

Nucleic Acid Targeting Moieties

As used herein, a "nucleic acid targeting moiety" is a nucleic acid that binds selectively to a target. In some embodiments, a nucleic acid targeting moiety is a nucleic acid that is associated with a particular organ, tissue, cell, extracellular matrix component, and/or intracellular compartment. In general, the targeting function of the aptamer is based on the three-dimensional structure of the aptamer. In some embodiments, binding of an aptamer to a target is typically mediated by the interaction between the two- and/or three-dimensional structures of both the aptamer and the target. In some embodiments, binding of an aptamer to a target is not solely based on the primary sequence of the aptamer, but depends on the three-dimensional structure(s) of the aptamer and/or target. In some embodiments, aptamers bind to their targets via complementary Watson-Crick base pairing which is interrupted by structures (e.g. hairpin loops) that disrupt base pairing.

One of ordinary skill in the art will recognize that any aptamer that is capable of specifically binding to a target can be used in accordance with the present invention. In some embodiments, aptamers to be used in accordance with the present invention may target cancer-associated targets. In some embodiments, aptamers to be used in accordance with the present invention may target tumor markers.

In certain embodiments, aptamers to be used in accordance with the present invention may target prostate cancer associated antigens, such as PSMA. Exemplary PSMA-targeting aptamers to be used in accordance with the present invention include, but are not limited to, the A10 aptamer, having a nucleotide sequence of 5'-GGGAGGACGAUGCG-GAUCAGCCAUGUUUACGUCACUCCUUGUCAAU CCUCAUCGGCAGACGACUCGCCCGA-3' (SEQ ID NO: 1) (Lupold et al, 2002, *Cancer Res*, 62:4029), the A9 aptamer, having nucleotide sequence of 5'-GGGAGGACGAUGCG-GACCGAAAAAGACCUGACUUCUAUACUAAGUC UACGUUCCCAGACGACUCGCCCGA-3' (SEQ ID NO: 2) (Lupold et al., 2002, *Cancer Res.*, 62:4029; and Chu et al., 2006, *Nuc. Acid Res.*, 34:e73), derivatives thereof, and/or characteristic portions thereof.

In some embodiments, a nucleotide sequence that is homologous to a nucleic acid targeting moiety may be used in accordance with the present invention. In some embodiments, a nucleotide sequence is considered to be "homologous" to a nucleic acid targeting moiety if it comprises fewer than 30, 25, 20, 15, 10, 5, 4, 3, 2, or 1 nucleic acid substitutions relative to the aptamer. In some embodiments, a nucleotide sequence is considered to be "homologous" to a nucleic acid targeting moiety if their sequences are at least 25%, 30%, 35%, 40%, 45%, 50%, 55%, 60%, 65%, 70%, 75%, 80%, 85%, 90%, 95%, or 99% identical. In some embodiments, a nucleic acid sequence is considered to be 35%, 40%, 45%, 50%, 55%, 60%, 65%, 70%, 75%, 80%, 85%, 90%, 95%, or 99% similar. Nucleic acids of the present invention (including nucleic acid targeting moieties and/or functional RNAs to be delivered, e.g., RNAi agents, ribozymes, tRNAs, etc., described in further detail below) may be prepared according to any available technique including, but not limited to, chemical synthesis, enzymatic synthesis, enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in molecular biology, v. 288 (Clifton, N.J.) Totowa, N.J.: Humana Press, 2005).

The nucleic acid that forms the nucleic acid targeting moiety may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid targeting moiety can be replaced with a hydrocarbon linker or a polyether linker provided that the binding affinity and selectivity of the nucleic acid targeting moiety is not substantially reduced by the substitution (e.g., the dissociation constant of the nucleic acid targeting moiety for the target should not be greater than about $1\times10^{-3}$ M).

It will be appreciated by those of ordinary skill in the art that nucleic acids in accordance with the present invention may comprise nucleotides entirely of the types found in naturally occurring nucleic acids, or may instead include one or more nucleotide analogs or have a structure that otherwise differs from that of a naturally occurring nucleic acid. U.S. Pat. Nos. 6,403,779; 6,399,754; 6,225,460; 6,127,533; 6,031,086; 6,005,087; 5,977,089; and references therein disclose a wide variety of specific nucleotide analogs and modifications that may be used. See Crooke, S. (ed.) *Antisense Drug Technology: Principles, Strategies, and Applications* (1st ed), Marcel Dekker; ISBN: 0824705661; 1st edition (2001) and references therein. For example, 2'-modifications include halo, alkoxy and allyloxy groups. In some embodiments, the 2'-OH group is replaced by a group selected from H, OR, R, halo, SH, NH$_2$, NR$_2$ or CN, wherein R is C$_1$-C$_6$ alkyl, alkenyl, or alkynyl, and halo is F, Cl, Br or I. Examples of modified linkages include phosphorothioate and 5'-N-phosphoramidite linkages.

Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleosides (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and S'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially affected. To give but one example, modifications may be located at any position of an aptamer such that the ability of the aptamer to specifically bind to the aptamer target is not substantially affected. The modified region may be at the 5'-end and/or the 3'-end of one or both strands. For example, modified aptamers in which approximately 1-5 residues at the 5' and/or 3' end of either of employed. The modification may be a 5' or 3' terminal modification. One or both nucleic acid strands may comprise at least 50% unmodified nucleotides, at least 80% unmodified nucleotides, at least 90% unmodified nucleotides, or 100% unmodified nucleotides.

Nucleic acids in accordance with the present invention may, for example, comprise a modification to a sugar, nucleoside, or internucleoside linkage such as those described in U.S. Patent Publications 2003/0175950, 2004/0192626, 2004/0092470, 2005/0020525, and 2005/0032733. The present invention encompasses the use of any nucleic acid having any one or more of the modification described therein. For example, a number of terminal conjugates, e.g., lipids such as cholesterol, lithocholic acid, aluric acid, or long alkyl branched chains have been reported to improve cellular uptake. Analogs and modifications may be tested using, e.g., using any appropriate assay known in the art, for example, to select those that result in improved delivery of a therapeutic agent, improved specific binding of an aptamer to an aptamer target, etc. In some embodiments, nucleic acids in accordance with the present invention may comprise one or more non-natural nucleoside linkages. In some embodiments, one or more internal nucleotides at the 3'-end, 5'-end, or both 3'- and 5'-ends of the aptamer are inverted to yield a such as a 3'-3' linkage or a 5'-5' linkage.

Protein Targeting Moieties

In some embodiments, a targeting moiety in accordance with the present invention may be a protein or peptide. In certain embodiments, peptides range from about 5 to 100, 10 to 75, 15 to 50, or 20 to 25 amino acids in size. In some embodiments, a peptide sequence a random arrangement of amino acids.

The terms "polypeptide" and "peptide" are used interchangeably herein, with "peptide" typically referring to a polypeptide having a length of less than about 100 amino acids. Polypeptides may contain L-amino acids, D-amino acids, or both and may contain any of a variety of amino acid modifications or analogs known in the art. Useful modifications include, e.g., terminal acetylation, amidation, lipidation, phosphorylation, glycosylation, acylation, farnesylation, sulfation, etc.

In another embodiment, the targeting moiety can be a targeting peptide or targeting peptidomimetic has a length of at most 50 residues. In a further embodiment, a nanoparticle of the invention contains a targeting peptide or peptidomimetic that includes the amino acid sequence AKERC (SEQ ID NO: 3), CREKA (SEQ ID NO: 4), ARYLQKLN (SEQ ID NO: 5) or AXYLZZLN (SEQ ID NO: 6), wherein X and Z are variable amino acids, or conservative variants or peptidomimetics thereof. In particular embodiments, the targeting moiety is a peptide that includes the amino acid sequence AKERC (SEQ ID NO: 3), CREKA. (SEQ ID NO: 4), ARYLQKLN (SEQ ID NO: 5) or AXYLZZLN (SEQ ID NO: 6), wherein X and Z are variable amino acids, and has a length of less than 20, 50 or 100 residues. The CREKA peptide is known in the art, and is described in U.S. Patent Application No. 2005/0048063, which is incorporated herein by reference in its entirety. The octapeptide AXYLZZLN (SEQ ID NO: 6) is described in Dinkla et al., The Journal of Biological Chemistry, Vol. 282, No. 26, pp. 18686-18693, which is incorporated herein by reference in its entirety.

In one embodiment, the targeting moiety is an isolated peptide or peptidomimetic that has a length of less than 100 residues and includes the amino acid sequence CREKA (Cys Arg Glu Lys Ala.) or a peptidomimetic thereof. Such an isolated peptide- or peptidomimetic can have, for example, a length of less than 50 residues or a length of less than 20 residues. In particular embodiments, the invention provides a peptide that includes the amino acid sequence CREKA and has a length of less than 20, 50 or 100 residues.

Moreover, the authors of The Journal of Biological Chemistry, Vol. 282, No. 26, pp. 18686-18693 describe a binding motif in streptococci that forms an autoantigenic complex with human collagen IV. Accordingly, any peptide, or conservative variants or peptidomimetics thereof, that binds or forms a complex with collagen IV, or the basement membrane of a blood vessel, can be used as a targeting moiety for the nanoparticles of the invention.

Exemplary proteins that may be used as targeting moieties in accordance with the present invention include, but are not limited to, antibodies, receptors, cytokines, peptide hormones, proteins derrived from combinatorial libraries (e.g. avimers, affibodies, etc.), and characteristic portions thereof.

In some embodiments, any protein targeting moiety can be utilized in accordance with the present invention. To give but a few examples, IL-2, transferrin, GM-CSF, a-CD25, a-CD22, TGF-a, folic acid, a-CEA, a-EpCAM scFV, VEGF, LHRH, bombesin, somatostin, Gal, α-GD2, α-EpCAM, α-CD20, M0v19, scFv, α-Her-2, and α-CD64 can be used to target a variety of cancers, such as lymphoma, glioma, leukemia, brain tumors, melanoma, ovarian cancer, neuroblastoma, folate receptor-expressing tumors, CEA-expressing tumors, EpCAM-expressing tumors, VEGF-expressing tumors, etc. (Eklund et al, 2005, *Expert Rev. Anticancer Ther.*, 5:33; Kreitman et al., 2000, *J. Clin. OncoL*, 18:1622; Kreitman et al., 2001, *N. Engl. J. Med*, 345:241; Sampson et al., 2003, *J. Neurooncol*, 65:27; Weaver et al., 2003, *J. Neurooncol*, 65:3; Leamon et al., 1993, *J. Biol. Chem.*, 268:24847; Leamon et al., 1994, *J. Drug Target.*, 2:101; Atkinson et al., 2001, *J. Biol. Chem.*, 276:27930; Frankel et al., 2002, *Clin. Cancer Res.*, 8:1004; Francis et al, 2002, *Br. J. Cancer,* 87:600; de Graaf et al., 2002, *Br. J. Cancer,* 86:811; Spooner et al., 2003, *Br. J. Cancer,* 88:1622; Liu et al, 1999, *J. Drug Target.*, 7:43; Robinson et al, 2004, *Proc. Natl. Acad. Sci., USA*, 101:14527; Sondel et al, 2003, *Curr. Opin. Investig. Drugs*, 4:696; Connor et al., 2004, *J. Immunother.*, 27:211; Gillies et al, 2005, *Blood*, 105:3972; Melani et al, 1998, *Cancer Res.*, 58:4146; Metelitsa et al, 2002, *Blood*, 99:4166; Lyu et al, 2005, *Mol Cancer Ther.*, 4:1205; and Hotter et al, 2001, *Blood*, 97:3138).

In some embodiments, protein targeting moieties can be peptides. One of ordinary skill in the art will appreciate that any peptide that specifically binds to a desired target can be used in accordance with the present invention. In some embodiments, peptides targeting tumor vasculature are antagonists or inhibitors of angiogenic proteins that include VEGFR (Binetruy-Tournaire et al, 2000, *EMBO J.*, 19:1525), CD36 (Reiher et al, 2002, *Int. J. Cancer,* 98:682) and Kumar et al, 2001, *Cancer Res.*, 61:2232) aminopeptidase N (Pasqualini et al, 2000, *Cancer Res.*, 60:722), and matrix metalloproteinases (Koivunen et al., 1999, *Nat. Biotechnol,* 17:768). For instance, ATWLPPR (SEQ ID NO: 7) peptide is a potent antagonist of VEGF (Binetruy-Tournaire et al, 2000, *EMBO j,* 19:1525); thrombospondin-1 (TSP-1) mimetics can induce apoptosis in endothelial cells (Reiher et al, 2002, *Int. J. Cancer,* 98:682); ROD-motif mimics (e.g. cyclic peptide ACDCRGDCFCG (SEQ ID NO: 8) and ROD peptidomimetic SCH 221153) block integrin receptors (Koivunen et al, 1995, *Biotechnology (NY)*, 13:265; and Kumar et al, 2001, *Cancer Res.*, 61:2232); NGR-containing peptides (e.g. cyclic CNGRC (SEQ ID NO: 9)) inhibit aminopeptidase N (Pasqualini et al, 2000, *Cancer Res.*, 60:722); and cyclic peptides containing the sequence of HWGF (SEQ ID NO: 10) (e.g. CTTHWGFTLC (SEQ ID NO: 11)) selectively inhibit MMP-2 and MMP-9 (Koivunen et al., 1999, *Nat. Biotechnol.*, 17:768); and a LyP-1 peptide has been identified (CGNKRTRGC (SEQ ID NO: 12)) which specifically binds to tumor lymphatic vessels and induces apoptosis of endothelial cells (Laakkonen et al, 2004, *Proc. Nail Acad. Sci., USA*, 101:9381).

In some embodiments, peptide targeting moieties include peptide analogs that block binding of peptide hormones to receptors expressed in human cancers (Bauer et al., 1982, *Life Sci.*, 31:1133). Exemplary hormone receptors (Reubi et al, 2003, *Endocr. Rev.*, 24:389) include (1) somatostatin receptors (e.g. octreotide, vapreotide, and lanretode) (Froidevaux et al, 2002, *Biopolymers,* 66:161); (2) bombesin/gastrin-releasing peptide (GRP) receptor (e.g. RC-3940 series) (Kanashiro et al, 2003, *Proc. Natl. Acad. Sci., USA,* 100:15836); and (3) LHRH receptor (e.g. Decapeptyf, Lupron®, Zoladex®, and Cetrorelix®) (Schally et al., 2000, *Prostate,* 45:158).

In some embodiments, peptides that recognize IL-11 receptor-a can be used to target cells associated with prostate cancer tumors (see, e.g., U.S. Patent Publication 2005/0191294).

In some embodiments, a targeting moiety may be an antibody and/or characteristic portion thereof. The term "antibody" refers to any immunoglobulin, whether natural or wholly or partially synthetically produced and to derivatives thereof and characteristic portions thereof. An antibody may be monoclonal or polyclonal. An antibody may be a member of any immunoglobulin class, including any of the human classes: IgG, IgM, IgA, IgD, and IgE. One of ordinary skill in the art will appreciate that any antibody that specifically binds to a desired target can be used in accordance with the present invention.

In some embodiments, antibodies that recognize PSMA can be used to target cells associated with prostate cancer tumors. Such antibodies include, but are not limited to, scFv antibodies A5, GO, G1, G2, and G4 and mAbs 3/B7, 3/F11, 3/A12, K7, K12, and D20 (Elsasser-Beile et al, 2006, *Prostate,* 66:1359); mAbs E99, J591, J533, and J415 (Liu et al, 1997, *Cancer Res.*, 57:3629; Liu et al, 1998, *Cancer Res.*, 58:4055; Fracasso et al., 2002, *Prostate,* 53:9; McDevitt et al, 2000, *Cancer Res.*, 60:6095; McDevitt et al., 2001, *Science,* 294:1537; Smith-Jones et al, 2000, *Cancer Res.*, 60:5237; Vallabhajosula of al., 2004, *Prostate,* 58:145; Bander er a/., 2003, J. C/ro/., 170:1717; Patri et al., 2004, *Bioconj. Chem.*, 15:1174; and U.S. Pat. No. 7,163,680); mAb 7E11-05.3 (Horoszewicz et al., 1987, *Anticancer Res.*, 7:927); antibody 7E11 (Horoszewicz et al, 1987, *Anticancer Res.*, 7:927; and U.S. Pat. No. 5,162,504); and antibodies described in Chang et al., 1999, *Cancer Res.*, 59:3192; Murphy et al., 1998, *J. UroL,* 160:2396; Grauer et al, 1998, *Cancer Res.*, 58:4787; and Wang era/., 2001, M J. Cancer, 92:871. One of ordinary skill in the art will appreciate that any antibody that recognizes and/or specifically binds to PSMA may be used in accordance with the present invention.

In some embodiments, antibodies which recognize other prostate tumor-associated antigens are known in the art and can be used in accordance with the present invention to target cells associated with prostate cancer tumors (see, e.g., Vihko et al, 1985, *Biotechnology in Diagnostics,* 131; Babaian et al, 1987, *J. UroL,* 137:439; Leroy et al., 1989, *Cancer,* 64:1;

Meyers et al, 1989, *Prostate,* 14:209; and U.S. Pat. Nos. 4,970,299; 4,902,615; 4,446,122 and Re 33,405; 4,862,851; 5,055,404). To give but a few examples, antibodies have been identified which recognize transmembrane protein 24P4C12 (U.S. Patent Publication 2005/0019870); calveolin (U.S. Patent Publications 2003/0003103 and 2001/0012890); L6 (U.S. Patent Publication 2004/0156846); prostate specific reductase polypeptide (U.S. Pat. No. 5,786,204; and U.S. Patent Publication 2002/0150578); and prostate stem cell antigen (U.S. Patent Publication 2006/0269557).

In some embodiments, protein targeting moieties that may be used to target cells associated with prostate cancer tumors include conformationally constricted dipeptide mimetics (Ding et al, 2004, *Org. Lett.,* 6:1805).

As used herein, an antibody fragment (i.e., characteristic portion of an antibody) refers to any derivative of an antibody which is less than full-length. In general, an antibody fragment retains at least a significant portion of the full-length antibody's specific binding ability. Examples of antibody fragments include, but are not limited to, Fab, Fab", F(ab')2, scFv, Fv, dsFv diabody, and Fd fragments.

An antibody fragment can be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multimolecular complex. A functional antibody fragment will typically comprise at least about 50 amino acids and more typically will comprise at least about 200 amino acids. In some embodiments, antibodies may include chimeric (e.g., "humanized") and single chain (recombinant) antibodies. In some embodiments, antibodies may have reduced effector functions and/or bispecific molecules. In some embodiments, antibodies may include fragments produced by a Fab expression library.

Single-chain Fvs (scFvs) are recombinant antibody fragments consisting of only the variable light chain (VL) and variable heavy chain (VH) covalently connected to one another by a polypeptide linker. Either VL or VH may comprise the $NH_2$-terminal domain. The polypeptide linker may be of variable length and composition so long as the two variable domains are bridged without significant steric interference. Typically, linkers primarily comprise stretches of glycine and serine residues with some glutamic acid or lysine residues interspersed for solubility.

Diabodies are dimeric scFvs. Diabodies typically have shorter peptide linkers than most scFvs, and they often show a preference for associating as dimers.

An Fv fragment is an antibody fragment which consists of one VH and one VL domain held together by noncovalent interactions. The term "dsFv" as used herein refers to an Fv with an engineered intermolecular disulfide bond to stabilize the VH-VL pair.

A Fab' fragment is an antibody fragment essentially equivalent to that obtained by reduction of the disulfide bridge or bridges joining the two heavy chain pieces in the F(ab')2 fragment. The Fab' fragment may be recombinantly produced.

A Fab fragment is an antibody fragment essentially equivalent to that obtained by digestion of immunoglobulins with an enzyme (e.g. papain). The Fab fragment may be recombinantly produced. The heavy chain segment of the Fab fragment is the Fd piece.

Carbohydrate Targeting Moieties

In some embodiments, a targeting moiety in accordance with the present invention may comprise a carbohydrate. To give but one example, lactose and/or galactose can be used for targeting hepatocytes.

In some embodiments, a carbohydrate may be a polysaccharide comprising simple sugars (or their derivatives) connected by glycosidic bonds, as known in the art. Such sugars may include, but are not limited to, glucose, fructose, galactose, ribose, lactose, sucrose, maltose, trehalose, cellbiose, mannose, xylose, arabinose, glucdronic acid, galactoronic acid, mannuronic acid, glucosamine, galatosatnine, and neuramic acid. In some embodiments, a carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, algin and alginic acid, starch, chitin, heparin, konjac, glucommannan, pustulan, heparin, hyaluronic acid, curdlan, and xanthan.

In some embodiments, the carbohydrate may be aminated, carboxylated, and/or sulfated. In some embodiments, hydropbilic polysaccharides can be modified to become hydrophobic by introducing a large number of side-chain hydrophobic groups. In some embodiments, a hydrophobic carbohydrate may include cellulose acetate, pullulan acetate, konjac acetate, amylose acetate, and dextran acetate.

Lipid Targeting Moieties

In some embodiments, a targeting moiety in accordance with the present invention may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid group may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

The targeting moiety can be conjugated to the polymeric matrix or amphiphilic component using any suitable conjugation technique. For instance, two polymers such as a targeting moiety and a biocompatible polymer, a biocompatible polymer and a poly(ethylene glycol), etc., may be conjugated together using techniques such as EDC-NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. The conjugation of such polymers, for instance, the conjugation of a poly(ester) and a poly(ether) to form a poly (ester-ether), can be performed in an organic solvent, such as, but not limited to, dichloromethane, acetonitrile, chloroform, dimethylformamide, tetrahydrofuran, acetone, or the like.

Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a targeting moiety) comprising an amine. For instance, a targeting moiety, such as an aptamer or peptide, may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. The conjugation reaction between the amine-containing moiety and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethysulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol.

A polymeric conjugate (i.e., a targeting moiety covalently bound to the polymeric component of the reverse micelle) of the present invention may be formed using any suitable conjugation technique. For instance, two compounds such as a targeting moiety and a biocompatible polymer, a biocompatible polymer and a poly(ethylene glycol), etc., may be conjugated together using techniques such as EDC-NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. The conjugation of such polymers, for instance, the conjugation of a poly(ester) and a poly(ether) to form a poly(ester-ether), can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a targeting moiety) comprising an amine. For instance, a targeting moiety, such as an aptamer, may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. The conjugation reaction between the amine-containing moiety (e.g., aptamer) and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethysulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol.

As a specific example, an aptamer may be prepared as a targeting moiety in a particle as follows. Carboxylic acid modified poly(lactide-co-glycolide) (PLGA-COOH) may be conjugated to an amine-modified heterobifunctional poly (ethylene glycol) ($NH_2$-PEG-COOH) to form a copolymer of PLGA-PEG-COOH. By using either an amine containing or an amine-modified aptamer ($NH_2$-Apt), a triblock polymer of PLGA-PEG-Apt may be formed by conjugating the carboxylic acid end of the PEG to the amine functional group on the aptamer. The multiblock polymer can then be used, for instance, as discussed below, e.g., for therapeutic applications.

Preparation of Polymer-Encapsulated Reverse Micelles

Another aspect of the invention is directed to systems and methods of producing such polymer-encapsulated reverse micelles. As mentioned, one aspect of the invention is directed to a method of developing polymer-encapsulated reverse micelles with desired properties, such as desired chemical, biological, or physical properties. In one set of embodiments, the method includes producing libraries of polymer-encapsulated reverse micelles having highly controlled properties, which can be formed by mixing together two or more polymers in different ratios. By mixing together two or more different polymers (e.g., copolymers, e.g., block copolymers) in different ratios and producing particles from the polymers (e.g., copolymers, e.g., block copolymers), particles having highly controlled properties may be formed. For example, one polymer (e.g., copolymer, e.g., block copolymer) may include a targeting moiety, while another polymer (e.g., copolymer, e.g., block copolymer) may be chosen for its biocompatibility and/or its ability to control immunogenicity of the resultant polymer-encapsulated reverse micelles.

Two major methods of forming nanoparticles that encapsulate nucleic acids currently exist. These involve: (1) forming water/oil/water double emulsions, which have the effect of dispersing the hydrophilic agent throughout the phase containing the polymer prior to polymer precipitation and nanoparticle formation using high frequency sonication and/or honiogenization, and (2) using unnatural cationic emulsifiers and condensing agents, typically cationic lipids, cationic polymers, or cationic small molecules, to disperse the negatively charged nucleic acid in the phase containing the polymer.

These methods are disfavored for a variety of reasons. In the case of the first method, the major limitations are: (1) loss of nucleic acid activity due to high shear denaturation and molecule damage, (2) low reproducibility of results, (3) low encapsulation yield, particularly for low molecular weight nucleic acids, and (4) low nucleic acid content per nanoparticle. These issues are a consequence of the physicochemical characteristics of the polymer and the nucleic acid, and as such, are difficult to overcome. In the case of the second method, the toxicity of cationic polymers, lipids, and small molecules have been well documented. These systems are disfavored due to the toxicity of the components, which are capable of non-selectively damaging the biological milieu of interest. In addition, this approach does not appreciate the effect of forming reverse micelles prior to the addition of polymer, which can potentially cause an undesirable competition in the nanoparticle formation process.

The disclosed invention overcomes the limitations imposed by the first method by effectively dispersing the therapeutic agent (e.g., nucleic acid) of interest into a fine nanosuspension of reverse micelles prior to nanoparticle formation, without the use of high frequency sonication or homogenization. The reverse micellization step effectively packages therapeutic agents (e.g., nucleic acids) by improving the thermodynamics of interaction between the nucleic acids and the biodegradable polymer, thereby improving the encapsulation yield and nucleic acid content per nanoparticle. The disclosed invention requires no high frequency sonication or homogenization, and therefore does not incur the losses that are common in methods that incorporate those techniques. The disclosed invention overcomes the toxicity issues in using cationic lipids, polymers, and small molecules by using non-toxic and/or naturally-occurring-uncharged and negatively charged lipids. The present invention involves forming reverse micelles prior to nanoprecipitation, thereby avoiding the potential competition that is a result of one-step procedures. The use of the nanoprecipitation method improves the reproducibility of results by making the desired nanoparticle a thermodynamically favored result.

Thus, in one set of embodiments, the polymer-encapsulated reverse micelles are formed by providing one or more solutions comprising one or more therapeutic agents (e.g., a nucleic acid) and amphiphilic components, and contacting them with certain solvents to produce a reverse micelle. A polymer is then added to the micelle solution, and this solution is then added to a different solvent to form a polymer-encapsulated reverse micelle.

For example, the therapeutic agent (e.g., nucleic acid) to be encapsulated is first incorporated into reverse micelles by mixing the agent with naturally derived and non-toxic amphipathic lipids in a volatile, water-miscible organic solvent. In one embodiment, the therapeutic agent to be encapsulated is a neucleic acid, including, but not limited to, natural or unnatural siRNAs, shRNAs, microRNAs, ribozymes, DNA plasmids, aptamers, antisense oligonucleotides, randomized oligonucleotides, or ribozymes. The amphipathic lipid can be, but is not limited to, one or a plurality of the following: phosphatidylcholine, lipid A, cholesterol, dolichol, shingosine, sphingomyelin, ceramide, cerebroside, sulfatide, glycosylceramide, phytosphingosine, phosphatidylethanolamine, phosphatidylglycerol, phosphatidylinositol, phosphatidylserine, cardiolipin, phophatidic acid, and lysophophatides. The volatile, water-miscible organic solvent can be, but is not limited to, tetrahydrofuran, acetone, acetonitrile, or dmethylformamide. The biodegradable polymer is added to this mixture after reverse micelle formation is complete. In a preferred embodiment, the biodegradable polymer can be, but is not limited to one or a plurality of the following: poly(D,L-lactic acid), poly(D,L-glycolic acid), poly(ε-caprolactone), their copolymers at various molar ratios, and their copolymers diblocked or multiblocked with poly(ethylene glycol). The resulting biodegradable polymer-reverse micelle mixture is combined with a polymer-insoluble hydrophilic non-solvent to form nanoparticles by the rapid diffusion of the solvent into the non-solvent and evaporation of the organic solvent. In a preferred embodiment, the polymer-insoluble hydrophilic non-solvent can be, but is not limited to one or a plurality of the following: water, ethanol, methanol, and mixtures thereof.

The methods of the invention can be used to create a library of polymer-encapsulated reverse micelles. By creating a library of such particles, particles having any desirable properties may be identified. For example, properties such as surface functionality, surface charge, size, zeta ($\zeta$) potential, hydrophobicity, ability to control immunogenicity, and the like, may be highly controlled. For instance, a library of particles may be synthesized, and screened to identify the particles having a particular ratio of polymers that allows the particles to have a specific density of moieties (e.g., aptamers) present on the surface of the particle. This allows particles having one or more specific properties to be prepared, for example, a specific size and a specific surface density of moieties, without an undue degree of effort. Accordingly, certain embodiments of the invention are directed to screening techniques using such libraries, as well as any particles identified using such libraries. In addition, identification may occur by any suitable method. For instance, the identification may be direct or indirect, or proceed quantitatively or qualitatively.

In another embodiment, the invention provides a method of preparing a polymer-encapsulated reverse micelle wherein the micelle has a ratio of ligand-bound polymer to non-functionalized polymer effective for the treatment of a disease, e.g., cancer, e.g., prostate cancer, wherein the hydrophilic, ligand-bound polymer is conjugated to a lipid that will self assemble with the hydrophobic polymer, such that the hydrophobic and hydrophilic polymers that constitute the nanoparticle are not covalently bound. "Self-assembly" refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties. For example, such a method comprises providing a first polymer that is reacted with a lipid, to form a polymer/lipid conjugate. The polymer/lipid conjugate is then reacted with a targeting moiety (e.g., an aptamer) to prepare a ligand-bound polymer/lipid conjugate; and mixing the ligand-bound polymer/lipid conjugate with a second, non-functionalized polymer, and the therapeutic agent; such that the stealth nanoparticle is formed. In certain embodiments, the first polymer is PEG, such that a lipid-terminated PEG is formed. In one embodiment, the lipid is of the Formula V, e.g., 2 distearoyl-sn-glycero-3-phosphoethanolamine (DSPE), and salts thereof, e.g., the sodium salt. The lipid-terminated PEG can then, for example, be mixed with PLGA to form a particle.

In some cases, a population of polymer-encapsulated reverse micelles may be present. For example, a population of particles may include at least 20 particles, at least 50 particles, at least 100 particles, at least 300 particles, at least 1,000 particles, at least 3,000 particles, or at least 10,000 particles. Various embodiments of the present invention are directed to such populations of particles. For instance, in some embodiments, the particles may each be substantially the same shape and/or size ("monodisperse"). For example, the particles may have a distribution of characteristic dimensions such that no more than about 5% or about 10% of the particles have a characteristic dimension greater than about 10% greater than the average characteristic dimension of the particles, and in some cases, such that no more than about 8%, about 5%, about 3%, about 1%, about 0.3%, about 0.1%, about 0.03%, or about 0.01% have a characteristic dimension greater than about 10% greater man the average characteristic dimension of the particles. In some cases, no more than about 5% of the particles have a characteristic dimension greater than about 5%, about 3%, about 1%, about 0.3%, about 0.1%, about 0.03%, or about 0.01% greater than the average characteristic dimension of the particles.

The library of particles can then be screened in some fashion to identify those polymer-encapsulated reverse micelles having one or more desired properties, for example, surface functionality, surface charge, size, zeta ($\zeta$) potential, hydrophobicity, ability to control immunogenicity, and the like. One or more of the macromolecules within the particles may include one or more polymers chosen to be biocompatible or biodegradable, one or more polymers chosen to reduce immunogenicity, and/or one or more targeting moieties. The macromolecules within the library may comprise some or all of these polymers, in any suitable combination (including, but not limited to, combinations in which a first polymer comprises a targeting moiety and a second polymer does not contain any of these species).

The nanoparticles described above may also contain therapeutic agents. Examples of therapeutic agents include, but are not limited to, a chemotherapeutic agent, a radioactive agent, a nucleic acid-based agent, a lipid-based agent, a carbohydrate based agent, a natural small molecule, or a synthetic small molecule.

Therapeutic Agents

According to the present invention, any agents ("payload"), including, for example, therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be delivered by the nanoparticles of the invention. Exemplary agents to be delivered in accordance with the present invention include, but are not limited to, small molecules (e.g. cytotoxic agents), nucleic acids (e.g., siRNA, RNAi, and mircoRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g., prostate cancer).

For instance, the targeting moiety may target or cause the particle to become localized at specific portions within a subject, and the payload may be delivered to those portions. In a particular embodiment, the drug or other payload is released in a controlled release manner from the particle and allowed to interact locally with the particular targeting site (e.g., a tumor). The term "controlled release" (and variants of that term) as used herein (e.g., in the context of "controlled-release system") is generally meant to encompass release of a substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

For example, a targeting portion may cause the particles to become localized to a tumor, a disease site, a tissue, an organ, a type of cell, etc. within the body of a subject, depending on the targeting moiety used. For example, a targeting moiety, e.g., an aptamer, may become localized to prostate cancer cells.

In particular embodiments, the agent to be delivered is a nucleic acid selected from the group consisting of natural or unnatural siRNAs, shRNAs, microRNAs, ribozymes, DNA plasmids, aptamers, antisense oligonucleotides, randomized oligonucleotides, or ribozymes.

In one embodiment, the reverse micelle particles of this invention will contain nucleic acids such as siRNA.

Preferably, the siRNA molecule has a length from about 10-50 or more nucleotides. More preferably, the siRNA molecule has a length from about 15-45 nucleotides. Even more preferably, the siRNA molecule has a length from about 19-40 nucleotides. Even more preferably, the siRNA molecule has a length of from about 21-23 nucleotides.

The siRNA of the invention preferably mediates RNAi against a target mRNA. The siRNA molecule can be designed such that every residue is complementary to a residue in the target molecule. Alternatively, one or more substitutions can be made within the molecule to increase stability and/or enhance processing activity of said molecule. Substitutions can be made within the strand or can be made to residues at the ends of the strand.

The target mRNA cleavage reaction guided by siRNAs is sequence specific. In general, siRNA containing a nucleotide sequence identical to a portion of the target gene are preferred for inhibition. However, 100% sequence identity between the siRNA and the target gene is not required to practice the present invention. Sequence variations can be tolerated including those that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

Moreover, not all positions of an siRNA contribute equally to target recognition. Mismatches in the center of the siRNA are most critical and essentially abolish target RNA cleavage. In contrast, the 3' nucleotides of the siRNA do not contribute significantly to specificity of the target recognition. Generally, residues at the 3' end of the siRNA sequence which is complementary to the target RNA (e.g., the guide sequence) are not critical for target RNA cleavage.

Sequence identity may readily be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad Sci. USA 87:2264-68, modified as in Karlin and Altschul (1993) Proc. Natl. Acad. Sci. USA 90:5873. Such an algorithm is incorporated into the BLAST programs (version 2.0) of Altschul, et al. (1990) J Mol Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389. A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between the siRNA and the portion of the target mRNA is preferred. Alternatively, the siRNA may be defined functionally as a nucleotide sequence (or oligonucleotide sequence) that is capable of hybridizing with a portion of the target mRNA transcript (e.g., 400 mM NaCl, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6($\log_{10}$[Na+])+0.41 (% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about or about equal to 10, 12, 15, 17, 20, 22, 25, 27, 30, 32, 35, 37, 40, 42, 45, 47 or 50 bases.

In one embodiment, the siRNA molecules of the present invention are modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the siRNAs in tissue culture medium.

In another embodiment of the present invention the siRNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar modified ribonucleotides, the 2'OH-group is replaced by a group selected from H, OR, R, halo, SH, SR, $NH_2$, NHR, $NR_2$ or $NO_2$, wherein R is C1-C6 alkyl, alkenyl or alkynyl and halo is F, Cl, Br or I.

Nucleotide analogues also include nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

RNA may be produced enzymatically or by partial/total organic synthesis, any modified ribonucleotide can be introduced by in vitro enzymatic or organic synthesis. In one embodiment, an siRNA is prepared chemically. Methods of synthesizing RNA molecules are known in the art, in particular, the chemical synthesis methods as described in Verina and Eckstein (1998), Annul Rev. Biochem. 67:99. In another embodiment, an siRNA is prepared enzymatically. For example, an siRNA can be prepared by enzymatic processing of a long, double-stranded RNA having sufficient complementarity to the desired target mRNA. Processing of long RNA can be accomplished in vitro, for example, using appropriate cellular lysates and siRNAs can be subsequently purified by gel electrophoresis or gel filtration. siRNA can then be denatured according to art-recognized methodologies. In an exemplary embodiment, siRNA can be purified from a mixture by extraction with a solvent or resin, precipitation, electrophoresis, chromatography, or a combination thereof. Alternatively, the siRNA may be used with no or a minimum of purification to avoid losses due to sample processing.

Alternatively, the siRNAs can also be prepared by enzymatic transcription from synthetic DNA templates or from DNA plasmids isolated from recombinant bacteria. Typically, phage RNA polymerases are used such as T7, T3 or SP6 RNA polyimerase (Milligan and Uhlenbeck (1989) Methods Enzyniol 180:51-62). The RNA may be dried for storage or dissolved in an aqueous solution. The solution may contain buffers or salts to inhibit annealing, and/or promote stabilization of the double strands.

Commercially available design tools and kits, such as those available from Ambion, Inc. (Austin, Tex.), and the Whitehead Institute of Biomedical Research at MIT (Cambridge, Mass.) allow for the design and production of siRNA. By way of example, a desired mRNA sequence can be entered into a sequence program that will generate sense and antisense target strand sequences. These sequences can then be entered into a program that determines the sense and antisense siRNA oligonucleotide templates. The programs can also be used to add, e.g., hairpin inserts or T1 promoter primer sequences. Kits also can then be employed to build siRNA expression cassettes.

In various embodiments, siRNAs are synthesized in vivo, in situ, and in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the siRNAs. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses siRNAs from a recombinant construct may be produced by introducing the construct into a zygote, an embryonic stem cell, or another multipotent cell derived from the appropriate organism.

In one embodiment, the target mRNA of the invention specifies the amino acid sequence of at least one protein such as a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2. CBL, CSFIR, ERBA, ERBB, EBRB2, ERBB2, ERBB3, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor proteins (e.g., APC, BRCA1, BRCA2, MADH4, MCC, NF 1, NF2, RB 1, TP53, and WTI); and enzymes (e.g., ACC synthases and oxidases, ACP desaturases and hydroxylases, ADPglucose pyrophorylases, acetylases and deacetylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases), proteins involved in tumor growth (including vascularization) or in metastatic activity or potential, including cell surface receptors and ligands as well as secreted proteins, cell cycle regulatory, gene regulatory, and apoptosis regulatory proteins, immune response, inflammation, complement, or clotting regulatory proteins.

As used herein, the term "oncogene" refers to a gene which stimulates cell growth and, when its level of expression in the cell is reduced, the rate of cell growth is reduced or the cell becomes quiescent. In the context of the present invention, oncogenes include intracellular proteins, as well as extracellular growth factors which may stimulate cell proliferation through autocrine or paracrine function. Examples of human oncogenes against which siRNA and morpholino constructs can designed include c-myc, c-myb, mdm2, PKA-I (protein kinase A type I), Abl-1, Bcl2, Ras, c-Raf kinase, CDC25 phosphatases, cyclins, cyclin dependent kinases (cdks), telomerase, PDGF/sis, erb-B, fos, jun, mos, and src, to name but a few. In the context of the present invention, oncogenes also include a fusion gene resulted from chromosomal translocation, for example, the Bcr/Abl fusion oncogene.

Further proteins include cyclin dependent kinases, c-myb, c-myc, proliferating cell nuclear antigen (PCNA), transforming growth factor-beta (TGF-beta), and transcription factors nuclear factor kappaB (NF-.kappa.B), E2F, HER-2/neu, PKA, TGF-alpha, EGFR, TGF-beta, IGFIR, P12, MDM2, BRCA, Bcl-2, VEGF, MDR, ferritin, transferrin receptor, IRE, C-fos, HSP27, C-raf and metallothionein genes.

The siRNA employed in the present invention can be directed against the synthesis of one or more proteins. Additionally or alternatively, there can be more than one siRNA directed against a protein, e.g., duplicate siRNA or siRNA that correspond to overlapping or non-overlapping target sequences against the same target protein. Accordingly, in one embodiment two, three, four or any plurality of siRNAs against the same target mRNA can be included in the nanoparticles of the invention. Additionally, several siRNAs directed against several proteins can be employed. Alternatively, the siRNA can be directed against structural or regulatory RNA molecules that do not code for proteins.

In a preferred aspect of the invention, the target mRNA molecule of the invention specifies the amino acid sequence of a protein associated with a pathological condition. For example, the protein may be a pathogen-associated protein (e.g., a viral protein involved in immunosuppression or immunoavoidance of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the invention specifies the amino acid sequence of an endogenous protein (i.e. a protein present in the genome of a cell or organism). In another embodiment, the target mRNA molecule of the invention specifies the amino acid sequence of a heterologous protein expressed in a recombinant cell or a genetically altered organism. In another embodiment, the target mRNA molecule of the invention specifies the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of said proteins and therapeutic benefits which may be obtained from said inhibition may be obtained.

In one embodiment, the nanoparticles of this invention comprises one or more siRNA molecules to silence a PDGF beta gene, Erb-B gene, Src gene, CRK gene, GRB2 gene, RAS gene, MEKK gene, INK gene, RAF gene, Erkl/2 gene, PCNA(p21) gene, MYB gene, JJN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, Skp2 gene, kinesin spindle protein gene, Bcr-Abl gene, Stat3 gene, cSrc gene, PKC gene, Bax gene, Bcl-2 gene, EGFR gene, VEGF gene, myc gene, NFKB gene, STAT3 gene, survivin gene, Her2/Neu gene, topoisomerase I gene, PLK1 gene, protein kinase 3 gene, CD31 gene, IGF-1 gene, topoisomerase II alpha gene, mutations in the p73 gene, mutations in the p21 (WAF 1/CIP 1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, mutations in the p53 tumor suppressor gene, mutations in the p53 family member DN-p63, mutations in the pRb tumor suppressor gene, mutations in the APC1 tumor suppressor gene, mutations in the BRCA1 tumor suppressor gene, mutations in the PTEN tumor suppressor gene, mLL fusiongene, BCRIABL fusion gene, TEL/AML1 fusion gene, EWS/FLI1 fusion gene, TLS/FUS1 fusion gene, PAX3/FKHR fusion gene, AML1/ETO fusion gene, alpha v-integrin gene, Fit-i receptor gene, tubulin gene, Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis B Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, plasmodium gene, a gene that is required for plasmodium gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chiamydia pneumoniae* gene, a gene that is required for *Chiamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-11 gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, 1-3 09 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCA7 gene, SCA8 gene, allele gene found in LOH cells, or one allele gene of a polymorphic gene. Examples of relevant siRNA molecules to silence genes and methods of making siRNA molecules can be found from commercial sources such as Dharmacon or from the following patent applications: US2005017667, WO2006066158, WO2006078278, U.S. Pat. No. 7,056,704, U.S. Pat. No. 7,078,196, U.S. Pat. No. 5,898,031, U.S. Pat. No. 6,107,094, EP 1144623, and EU 1144623, all of which are incorporated herein by reference in their entireties. While a number of specific gene silencing targets are listed, this list is merely illustrative and other siRNA molecules could also be used with the nanoparticles of this invention.

In one embodiment, the nanoparticles of this invention comprise an siRNA molecule having RNAi activity against an RNA, wherein the siRNA molecule comprises a sequence complementary to any RNA having coding or non-encoding sequence, such as those sequences referred to by GenBank Accession Nos. described in Table V of PCT/US03/05028 (International PCT Publication No. WO 03/4654) or otherwise known in the art.

In one embodiment, the nanoparticles of this invention comprise an siRNA molecule which silences the vascular endothelial growth factor gene. In another embodiment, the nanoparticles of this invention comprise an siRNA molecule which silences the vascular endothelial growth factor receptor gene.

In another embodiment, the nanoparticles of this invention comprise an siRNA molecule, wherein the sequence of the siRNA molecule is complementary to tumor-related targets, including, but not limited to, hypoxia-inducible factor-1 (HIF-1), which is found in human metastatic prostate PC3-M cancer cells (*Mol Carcinog.* 2008 Jan. 31 [Epub ahead of print]); the HIF-1 downstream target gene (*Mol Carcinog.* 2008 Jan. 31 [Epub ahead of print]), mitogen-activated protein kinases (MAPKs), hepatocyte growth factor (HGF), interleukin 12p70 (IL12), glucocorticoid-induced tumor necrosis factor receptor (GITR), intercellular adhesion molecule 1 (ICAM-1), neurotrophin-3 (NT-3), interleukin 17 (IL17), interleukin 18 binding protein a (IL18 Bpa) and epithelial-neutrophil activating peptide (ENA78) (see, e.g., "Cytokine profiling of prostatic fluid from cancerous prostate glands identifies cytokines associated with extent of tumor and inflammation", *The Prostate* Early view Published Online: 24 Mar. 2008); PSMA (see, e.g., "Cell-Surface labeling and internalization by a fluorescent inhibitor of prostate-specific membrane antigen" *The Prostate* Early view Published Online: 24 Mar. 2008); Androgen receptor (AR), keratin, epithelial membrane antigen, EGF receptor, and E cadherin (see, e.g., "Characterization of PacMetUT1, a recently isolated human prostate cancer cell line"); peroxisomes proliferators-activated receptor γ (PPARγ; see e.g., *The Prostate* Volume 68, Issue 6, Date: 1 May 2008, Pages: 588-598); the receptor for advanced glycation end products (RAGE) and the advanced glycation end products (AGE), (see, e.g., "V domain of RAGE interacts with AGEs on prostate carcinoma cells" *The Prostate* Early view Published Online: 26 Feb. 2008); the receptor tyrosine kinase erb-B2 (Her2/neu), hepatocyte growth factor receptor (Met), transforming growth factor-beta 1 receptor (TGFβR1), nuclear factor kappa B (NFκB), Jagged-1, Sonic hedgehog (Shh), Matrix metalloproteinases (MMPs, esp. MMP-7), Endothelin receptor type A ($ET_A$), Endothelin-1 (ET-1), Nuclear receptor subfamily 3, group C, member 1 (NR3C1), Nuclear receptor co-activator 1 (NCOA1), NCOA2, NCOA3, E1A binding protein p300 (EP300), CREB binding protein (CREBBP), Cyclin G associated kinase (GAK), Gelsolin(GSN), Aldo-keto reductase family 1, member C1 (AKR1C1), AKR1C2, AKR1C3, Neurotensin(NTS), Enolase 2(ENO2), Chromogranin B (CHGB, secretogranin 1), Secretagogin (SCGN, or EF-hand calcium binding protein), Dopa decarboxylase (DDC, or aromatic L-amino acid decarboxylase), steroid receptor co-activator-1 (SRC-1), SRC-2 (a.k.a. TIF2), SRC-3 (a.k.a. AIB-1) (see, e.g., "Longitudinal analysis of androgen deprivation of prostate cancer cells identifies pathways to androgen independence" *The Prostate* Early view Published Online: 26 Feb. 2008); estrogen receptors (ERα, ERβ or GPR30) (see, e.g., *The Prostate* Volume 68, Issue 5, Pages 508-516); the melanoma cell adhesion molecule (MCAM) (see, e.g., *The Prostate* Volume 68, Issue 4, Pages 418-426; angiogenic factors (such as vascular endothelial growth factor (VEGF) and erythropoietin), glucose transporters (such as GLUT1), BCL2/adenovirus E1B 19 kDa interacting protein 3 (BNIP3) (see, e.g., *The Prostate* Volume 68, Issue 3, Pages 336-343); types 1 and 2 5α-reductase (see, e.g., *The Journal of Urology* Volume 179, Issue 4, Pages 1235-1242); ERG and ETV1, prostate-specific antigen (PSA), prostate-specific membrane antigen (PSMA), prostate stem cell antigen (PSCA), α-Methylacyl coenzyme A racemase (AMACR), $PCA3^{DD3}$, glutathione-S-transferase, pi 1 (GSTP1), p16, ADP-ribosylation factor (ARF), O-6-methylguanine-DNA methyltransferase (MGMT), human telomerase reverse transcriptase (hTERT), early prostate cancer antigen (EPCA), human kallikrein 2 (HK2) and hepsin (see, e.g., *The Journal of Urology* Volume 178, Issue 6, Pages 2252-2259); bromodomain containing 2 (BRD2), eukaryotic translation initiation factor 4 gamma, 1 (eIF4G1), ribosomal protein L13a (RPL13a), and ribosomal protein L22 (RPL22) (see, e.g., *N Engl J Med* 353 (2005), p. 1224); HER2/neu, Derlin-1, ERBB2, AKT, cyclooxygenase-2 (COX-2), PSMD3, CRKRS, PERLD1, and C17ORF37, PPP4C, PARN, ATP6V0C, C16orf14, GBL, HAGH, ITFG3, MGC13114, MRPS34, NDUFB10, NMRAL1, NTHL1, NUBP2, POLR3K, RNPS1, STUB1, TBL3, and USP7. All of the references described herein are incorporated herein by reference in their entireties.

Thus, in one embodiment, the invention comprises a nanoparticle comprising a targeting moiety (e.g., PSMA ligand), a biodegradable polymer, a stealth polymer, and an siRNA molecule wherein the siRNA molecule is encapsulated within a reverse micelle. In one embodiment, the invention comprises a nanoparticle comprising a targeting moiety (e.g., PSMA ligand), a biodegradable polymer, a stealth component, and an siRNA molecule that silences the vascular endothelial growth factor gene, wherein the siRNA molecule is encapsulated within a reverse micelle. In one embodiment, the invention comprises a nanoparticle comprising a targeting moiety (e.g., PSMA ligand), a biodegradable polymer, a stealth component, and an siRNA molecule that silences the vascular endothelial growth factor receptor gene, wherein the siRNA molecule is encapsulated within a reverse micelle. In another embodiment, the invention comprises a nanoparticle comprising a targeting moiety (e.g., PSMA ligand), PLGA, polyethylene glycol, and an siRNA molecule, wherein the siRNA molecule is encapsulated within a reverse micelle. In one embodiment, the invention comprises a nanoparticle comprising a targeting moiety (e.g., PSMA ligand), a biodegradable polymer, a stealth component, and an siRNA molecule wherein the nanoparticle can selectively accumulate in the prostate or in the vascular endothelial tissue surrounding a cancer, wherein the siRNA molecule is encapsulated within a reverse micelle. In one embodiment, the invention comprises a nanoparticle comprising a targeting moiety (e.g., PSMA ligand), a biodegradable polymer, a stealth component, and an siRNA molecule wherein the nanoparticle can selectively accumulate in the prostate or in the vascular endothelial tissue surrounding a cancer and wherein the nanoparticle can be endocytosed by a PSMA expressing cell, wherein the siRNA molecule is encapsulated within a reverse micelle.

In one embodiment, the invention comprises a nanoparticle comprising one or a plurality of the following: natural or unnatural siRNAs, shRNAs, microRNAs, ribozymes, DNA enzymes, aptamers, antisense oligonucleotides, randomized oligonucleotides, DNA plasmids, etc. In another embodiment, the encapsulated nucleic acids include, but are not limited to, noncoding RNAs, for example, rRNA, snRNA, snoRNA and tRNA, etc. In certain embodiments, the encapsulated nucleic acids are small interfering RNAs or short interfering RNAs (siRNAs), referring to an RNA (or RNA analog) comprising between about 10-50 nucleotides (or nucleotide analogs) which is capable of directing or mediating RNA interference. In some preferred embodiments, the targets of RNA interference include, for example, the target genes exemplified in this invention.

In other embodiments, the encapsulated nucleic acids are natural or unnatural short hairpin RNAs (shRNAs) capable of inducing RNA interference with a stable knockdown, by expressing mimics of micro RNAs (miRNAs) from RNA polymerase II or III promoters (e.g., as described in "Unlocking the potential of the human genome with RNA interference" *Nature* 431, 371-378). In one preferred embodiment, shRNAs typically have stems ranging from 19 to 29 nucleotides in length, and with various degrees of structural similarity to nature miRNAs. In another preferred embodiment, shRNAs are expressed under Pol III promoter without immunostimulatory effects as siRNAs do (e.g., as described in "Stable expression of shRNAs in human CD34+ progenitor cells can avoid induction of interferon responses to siRNAs in vitro" *Nature Biotechnology* 24, 566-571). In one embodiment, the shRNA is expressed in commercially available vectors, e.g., from OriGene Technologies, Inc., which are based on a HuSH pRS plasmid vector which contains both 5 and 3 LTRs of Moloney murine leukemia virus (MMLV) that flank the puromycin marker and the U6-shRNA expression cassette. In one preferred embodiment, the shRNA expression cassette consists of a 21 bp target gene specific sequence, a 10 bp loop, another 21 bp reverse complementary sequence, and a termination sequence to terminate the transcription by RNA Pol III, all under a human U6 promoter. In one preferred embodiment, the 21 bp gene-specific sequence is sequence-verified to ensure its match to the target gene, which includes, for example, the target genes of siRNAs described in this invention.

In some embodiments, the encapsulated nucleic acids are natural or unnatural miRNAs, which are isolated from an organism or synthesized by standard techniques, respectively. In one embodiment, a miRNA is a single-stranded RNA of typically 19-25 nucleotides length, also referred to as a mature miRNA. In one preferred embodiment, the miRNAs act as post-transcriptional regulators of gene expression during cancer or tumor formation by base-pairing with their target mRNAs. In one embodiment, the miRNAs are encoded in a DNA plasmid and transfected into the cell. In one preferred embodiment, the target genes of the miRNAs include the target genes of siRNA described in this invention, for example, cytokines, proto-oncogenes, oncogenes (e.g., myc, ras, etc.) and other disease markers.

In some embodiments, the encapsulated nucleic acids are natural or unnatural ribozymes. In one embodiment, ribozyme molecules are designed to catalytically cleave target mRNA transcripts (e.g., as described in PCT International Publication WO90/11364; Sarver et al., 1990, *Science* 247: 1222-1225 and U.S. Pat. No. 5,093,246, which are incorporated herein in their entireties). In one preferred embodiment, hammerhead ribozymes are used to destroy target mRNAs at locations dictated by flanking regions that form complementary base pairs with the target mRNA. The construction and production of hammerhead ribozymes is well known in the art and is described more fully in Haseloff and Gerlach, 1988, *Nature,* 334:585-591. In other embodiments, the ribozymes also include RNA endoribonucleases ("Cech-type ribozymes") such as the one which occurs naturally in Tetrahymena thermophia (known as the IVS, or L-19 IVS RNA) (e.g. as described in International patent application No. WO88/04300).

In some embodiments, the encapsulated nucleic acids are natural or unnatural DNA enzymes. In one preferred embodiments, the DNA enzymes include two basic types, as identified by Santoro and Joyce (see, for example, U.S. Pat. No. 6,110,462). In some embodiments, the DNA enzymes are designed to specifically recognize and cleave a target nucleic acid. The target nucleic acid can be identified by one of skill in the art, using the same approach as outlined for siRNA. In one preferred embodiment, the unique or substantially sequence is a G/C rich of approximately 18 to 22 nucleotides.

In some embodiments, the encapsulated nucleic acids are natural or unnatural aptamers. In one preferred embodiment, the aptamers are nucleic acid molecules specifically binding to molecules through interactions other than classic Watson-Crick base pairing. In one embodiment, the aptamers are generated for proteins including growth factors, transcription factors, enzymes, immunoglobulins, and receptors (see, for example, U.S. patent Ser. No. 10/980,211). In one preferred embodiment, the aptamers are 10-15 kDa in size (30-45 nucleotides), bind their targets with sub-nanomolar affinity, and discriminate against closely related targets (e.g. proteins in the same gene family). The target selection for aptamers is well known in the art and includes, for example, the target genes of siRNAs described in this invention.

In some embodiments, the encapsulated nucleic acids are natural or unnatural antisense oligonucleotides. In one preferred embodiment, the antisense oligonucleotide is an isolated, synthetic, substantially pure, or recombinant polynucleotide having a sequence that is at least about 10 nucleotides in length to at least about 100 nucleotides in length. This polynucleotide comprises a sequence exactly complementary or identical to a contiguous sequence of a nucleic acid encoding an endogenous protein, or a mutated protein in the target cell. The target of the antisense oligonucleotides includes, for example, cytokines, proto-oncogenes, oncogenes (e.g., myc, ras, etc.) and other cancer or tumor-related genes, including the target genes of siRNA described in this invention. (see, for example, U.S. patent Ser. No. 10/637,443). The designing for antisense oligonucleotides is well known in the art.

In some embodiments, the encapsulated nucleic acids are randomized oligonucleotides. In one preferred embodiment, the randomized oligonucleotides are designed to consist essentially of one or more oligonucleotides capable of binding a DNA-binding protein or RNA primers in the target cell, thereby treating the cancer or tumor. The designing for randomized oligonucleotides is well known in the art and described, for example, in U.S. patent application Ser. No. 10/613,390).

In some embodiments, the encapsulated nucleic acids are DNA plasmids. In one preferred embodiments, the DNA plasmids are vectors to transport another nucleic acid to which it has been linked, achieve extra-chromosomal replication and/or expression of nucleic acid to which they are linked in a host cell (e.g., a cell targeted by targeted particles of the present invention). In some embodiments, the DNA plasmids can achieve integration into the genome of the host cell. In some embodiments, the DNA plasmids are used to direct protein and/or RNA expression. In one embodiment, the protein and/or RNA to be expressed is not normally expressed by the cell. In another embodiment, the protein and/or RNA to be expressed is normally expressed by the cell, but at lower levels than it is expressed when the plasmid has not been delivered to the cell. In one preferred embodiment, the DNA plasmids are designed to express siRNAs, shRNAs, miRNAs, ribozymes, DNA enzymes, apatamers, antisense oligonucleotides or randomized oligonucleotides described in the present invention.

In another embodiment, the nucleic acid (e.g. siRNA, shRNA, miRNA, etc.) that is incorporated into the nanoparticle of the invention are those that treat prostate cancer, such as those disclosed in U.S. patent application Ser. No. 11/021,159 (siRNA sequence is complementary to gaaggccagu uguauggac (SEQ ID NO: 13)), and U.S. application Ser. No. 11/349,473 Both of these references are incorporated herein by reference in their entirety.

In another embodiment, the therapeutic agents of the nanoparticles of the invention include RNAs that can be used to treat cancer, such as anti-sense mRNAs and microRNAs. Examples of microRNAs that can be used as therapeutic agents for the treatment of cancer include those disclosed in Nature 435 (7043): 828-833; Nature 435 (7043): 839-843; and Nature 435 (7043): 834-838, all of which are incorporated herein by reference in their entireties.

Once the inventive conjugates have been prepared, they may be combined with pharmaceutical acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc.

Methods of Treatment

In some embodiments, targeted particles in accordance with the present invention may be used to treat, alleviate, ameliorate, relieve, delay onset of, inhibit progression of, reduce severity of, and/or reduce incidence of one or more symptoms or features of a disease, disorder, and/or condition. In some embodiments, the targeted nanoparticles of the invention can be used to treat cancer, e.g., prostate or breast cancer, and/or cancer cells, e.g., prostate or breast cancer cells in a subject in need thereof. In other embodiments, the targeted nanoparticles of the invention can be used to treat atherosclerotic plaques, restenosis, and atherosclerosis in a subject in need thereof.

The term "subject" is intended to include organisms, e.g., prokaryotes and eukaryotes, which are capable of suffering from or afflicted with a disease or disorder. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a disease or disorder.

The term "cancer" includes pre-malignant as well as malignant cancers. Cancers include, but are not limited to, prostate, gastric cancer, colorectal cancer, skin cancer, e.g., melanomas or basal cell carcinomas, lung cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. "Cancer cells" can be in the form of a tumor, exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect of the invention, a method for the treatment of cancer (e.g. breast or prostate cancer) is provided. In some embodiments, the treatment of cancer comprises administering a therapeutically effective amount of inventive targeted particles to a subject in need thereof, in such amounts and for such time as is necessary to achieve the desired result. In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In one aspect of the invention, a method for administering inventive compositions to a subject suffering from cancer (e.g. breast or prostate cancer) is provided. In some embodiments, particles to a subject in such amounts and for such time as is necessary to achieve the desired result (i.e., treatment of cancer). In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In other embodiments, the nanoparticles of the present invention can be used to inhibit the growth of cancer cells, e.g., prostate or breast cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

The present invention is also directed, in part, to the discovery that a collagen IV alpha-2 chain related polypeptide can act as a receptor for the CREKA (SEQ ID NO: 4) tumor targeting peptide. Collagens are a major component of the extracellular matrix (ECM), an interconnected molecular network providing mechanical support for cells and tissues and regulating biochemical and cellular processes such as adhesion, migration, gene expression and differentiation (see, e.g., U.S. Patent Application No. 2005/0048063, which is incorporated herein by reference in its entirety). In higher animals, at least 19 distinct collagen types differing in their higher order structures and functions have been identified based on the presence of the characteristic collagen triple-helix structure. The collagens are sometimes categorized into the fibrillar and nonfibrillar collagens. The fibrillar (interstitial) collagens include types I, II, III, V and XI, while the nonfibrillar collagens include types IV, VI, IX, X, XI, XII, XIV and XIII.

Targeting moieties useful in the invention include those which selectively target tumor vasculature and selectively bind non-helical collagen. Targeting moieties include those which selectively target to tumor vasculature and selectively bind collagen IV, and those which selectively target tumor vasculature and selectively bind denatured collagen IV in preference to native collagen IV. Such moieties include, but are not limited to, AKERC (SEQ ID NO: 3), CREKA (SEQ ID NO: 4), ARYLQKLN (SEQ ID NO: 5) or AXYLZZLN (SEQ ID NO: 6), wherein X and Z are variable amino acids.

As such, the nanoparticles of the invention can be used for the treatment of vulnerable plaques in a subject in need thereof.

In a preferred embodiment, the nanoparticles of the invention can be delivered to or near a vulnerable plaque, particularly when the targeting moiety is a peptide that targets the basement membrane of a blood vessel (e.g., CREKA), using a medical device such as a needle catheter, drug eluding stent or stent graft. Such devices are well known in the art, and are described, for example, in U.S. Pat. No. 7,008,411, which is incorporated herein by reference in its entirety. In one embodiment, a drug eluting stent and/or needle catheter may be implanted at the region of vessel occlusion that may be upstream from a vulnerable plaque region. A medical device, such as a drug eluting stent, needle catheter, or stent graft may be used to treat the occlusive atherosclerosis (i.e., non-vulnerable plaque) while releasing the nanoparticle of the invention to treat a vulnerable plaque region distal or downstream to the occlusive plaque. The nanoparticle may be released slowly over time.

The nanoparticles of the invention can also be delivered to a subject in need thereof using the Genie™ balloon catheter available from Acrostak (http://www.acrostak.com/genie_en.htm). The nanoparticles of the invention can also be delivered to a subject in need thereof using delivery devices that have been developed for endovascular local gene transfer such as passive diffusion devices (e.g., double-occlusion balloon, spiral balloon), pressure-driven diffusion devices (e.g., microporous balloon, balloon-in-balloon devices, double-layer channeled perfusion balloon devices, infusion-sleeve catheters, hydrogel-coated balloons), and mechanically or electrically enhanced devices (e.g., needle injection catheter, iontophoretic electric current-enhanced balloons, stent-based system), or any other delivery system disclosed in Radiology 2003; 228:36-49, or Int J Nanomedicine 2007; 2(2):143-61, which are incorporated herein by reference in their entireties.

Pharmaceutical Compositions

As used herein, the term "pharmaceutically acceptable carrier" means a non-toxic, inert solid, semi-solid or liquid filler, diluent, encapsulating material or formulation auxiliary of any type. Remington's Pharmaceutical Sciences. Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. If filtration or other terminal sterilization methods are not feasible, the formulations can be manufactured under aseptic conditions.

The pharmaceutical compositions of this invention can be administered to a patient by any means known in the art including oral and parenteral routes. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles of the present invention are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be suppositories which can be prepared by mixing the inventive conjugate with suitable non-irritating excipients or carriers such as cocoa butter, polyethylene glycol, or a suppository wax which are solid at ambient temperature but liquid at body temperature and therefore melt in the rectum or vaginal cavity and release the inventive conjugate.

Dosage forms for topical or transdermal administration of an inventive pharmaceutical composition include ointments, pastes, creams, lotions, gels, powders, solutions, sprays, inhalants, or patches. The inventive conjugate is admixed under sterile conditions with a pharmaceutically acceptable carrier and any needed preservatives or buffers as may be required. Ophthalmic formulations, ear drops, and eye drops are also contemplated as being within the scope of this invention. The ointments, pastes, creams, and gels may contain, in addition to the inventive conjugates of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof. Transdermal patches have the added advantage of providing controlled delivery of a compound to the body. Such dosage forms can be made by dissolving or dispensing the inventive conjugates in a proper medium. Absorption enhancers can also be used to increase the flux of the compound across the skin. The rate can be controlled by either providing a rate controlling membrane or by dispersing the inventive conjugates in a polymer matrix or gel.

Powders and sprays can contain, in addition to the inventive conjugates of this invention, excipients such as lactose, talc, silicic acid, aluminum hydroxide, calcium silicates, and polyamide powder, or mixtures thereof. Sprays can additionally contain customary propellants such as chlorofluorohydrocarbons.

When administered orally, the inventive nanoparticles can be, but are not necessarily, encapsulated. A variety of suitable encapsulation systems are known in the art ("Microcapsules and Nanoparticles in Medicine and Pharmacy," Edited by Doubrow, M., CRC Press, Boca Raton, 1992; Mathiowitz and Langer J. Control. Release 5:13, 1987; Mathiowitz et al. Reactive Polymers 6:275, 1987; Mathiowitz et al. J. Appl. Polymer Sci. 35:755, 1988; Langer Ace. Chem. Res. 33:94, 2000; Langer J. Control. Release 62:7, 1999; Uhrich et al. Chem. Rev. 99:3181, 1999; Zhou et al. J. Control. Release 75:27, 2001; and Hanes et al. Pharm. Biotechnol. 6:389, 1995). The inventive conjugates may be encapsulated within biodegradable polymeric microspheres or liposomes. Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters), and other biodegradable polyesters. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides.

Pharmaceutical compositions for oral administration can be liquid or solid. Liquid dosage forms suitable for oral administration of inventive compositions include pharmaceutically acceptable emulsions, microemulsions, solutions, suspensions, syrups, and elixirs. In addition to an encapsulated or unencapsulated conjugate, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants, wetting agents, emulsifying and suspending agents, sweetening, flavoring, and perfuming agents. As used herein, the term "adjuvant" refers to any compound which is a nonspecific modulator of the immune response. In certain embodiments, the adjuvant stimulates the immune response. Any adjuvant may be used in accordance with the present invention. A large number of adjuvant compounds is known in the art (Allison Dev. Biol. Stand. 92:3-11, 1998; Unkeless et al. Annu. Rev. Immunol. 6:251-281, 1998; and Phillips et al. Vaccine 10:151-158, 1992).

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

It will be appreciated that the exact dosage of the targeted reverse micelle particle is chosen by the individual physician in view of the patient to be treated, in general, dosage and administration are adjusted to provide an effective amount of the targeted particle to the patient being treated. As used herein, the "effective amount" of a targeted particle refers to the amount necessary to elicit the desired biological response. As will be appreciated by those of ordinary skill in this art, the effective amount of targeted particle may vary depending on such factors as the desired biological endpoint, the drug to be delivered, the target tissue, the route of administration, etc. For example, the effective amount of targeted particle containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles of the invention may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions of the present invention will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

The present invention also provides any of the above-mentioned compositions in kits, optionally with instructions for administering any of the compositions described herein by any suitable technique as previously described, for example, orally, intravenously, pump or implantable delivery device, or via another known route of drug delivery. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, but can also include the composition of the invention and instructions of any form that are provided in connection with the composition in a manner such that a clinical professional will clearly recognize that the instructions are to be associated with the specific composition.

The kits described herein may also contain one or more containers, which may contain the inventive composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the nanoparticle and the mode of use or administration. Suitable solvents for drug compositions are well known, for example as previously described, and are available in the literature. The solvent will depend on the nanoparticle and the mode of use or administration.

The invention also involves, in another aspect, promotion of the administration of any of the nanoparticles described herein. In some embodiments, one or more compositions of the invention are promoted for the prevention or treatment of various diseases such as those described herein via administration of any one of the compositions of the present invention. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

EXAMPLES

The invention is further illustrated by the following examples. The examples should not be construed as further limiting.

Preparation of Polymer-Encapsulated Reverse Micelles

In this example, an anti-polo-like kinase 1 siRNA (anti-PLK1) can be resuspended in water at 1 mg/mL. Fifty microliters of this solution can be mixed with 1 mL of a tetrahydrofuran solution containing lecithin (a commercially available plant-derived mixture of glycolipids, triglycerides, and phospholipids) at 0.1 mg/mL to form lecithin-anti-PLK1 reverse micelles. These reverse micelles can be added to a 1 mL solution containing 5 mg/mL of poly(D,L-lactic-co-glycolic acid)-block-poly(ethylene glycoi-block-A10 anti-PSMA aptamer) (PLGA-PEG-Apt) triblock copolymer dissolved in tetrahydrofuran. This mixture of lecithin-anti-PLK1 reverse micelles and PLGA-PEG-Apt can be added dropwise to 3 mL of a DNase/RNase free water solution to form anti-PLK1-containing nanoparticles that present anti-PSMA aptamers on the surface by the nanoprecipitation method. This procedure would yield nanoparticles targeting an anti-PLK1 siRNA to PSMA-expressing cells, such as LNCaP prostate adenocarcinomas, to produce selective cell killing.

In a second embodiment, DNA oligonucleotides of known sequence may be encapsulated efficiently into nanoparticles of different physicochemical properties, such that each distinct nanoparticle formulation contains a known and unique oligonucleotide. The nanoparticles of different physicochemical characteristics may then be screened in parallel either in vitro or in vivo for preferential cell uptake or tumor targeting, respectively, by collecting the cells or the tumor and assaying for the total content of each oligonucleotide by ELISA, sandwich capture assay, or quantitative RT-PCR. Nanoparticles of biodegradable polymers may then be selected for a particular application by correlating the levels of oligonucleotide present with the levels of nanoparticles present in the targeted location.

Encapsulation efficiency is determined by taking a known amount of DNA, encapsulating it into a nanoparticle, removing any unencapsulated DNA by filtration, lysing the nanoparticle, then detecting the amount of DNA that was encapsulated by measuring its absorbance of light at 260 nm. The encapsulation efficiency is calculated by taking the amount of DNA that was encapsulated, then dividing it by the original amount of DNA. Stated alternatively, it is the fraction of initial DNA that is successfully encapsulated.

Zeta potential is determined by Quasi-elastic laser light scattering with a ZetaPALS dynamic light scattering detector (Brookhaven Instruments Corporation, Holtsville, N.Y.; 15 mW laser, incident beam=676 nm).

FIG. 1 demonstrates the effect of amphipathic lipid concentration on encapsulation particle size.

Figure 2:
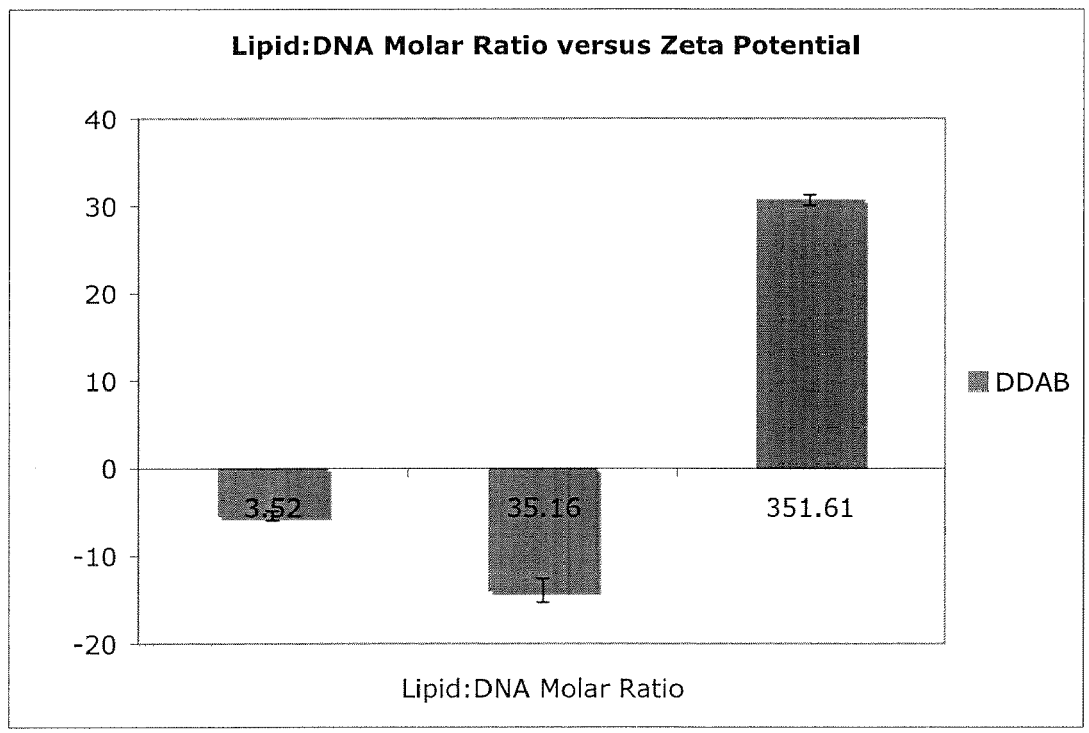
FIG. 2 demonstrates the effect of amphipathic lipid concentration on particle zeta potential.

FIG. 2 demonstrates the effect of amphipathic lipid concentration on particle zeta potential. PLGA-PEG and DDAB (dimethyldiotadecylammonium bromide), a cationic lipid, were used as the polymer and lipid in the reverse micelle nanoprecipitation protocol. As the ratio of lipid:DNA is increased, one can see that there is a point between the ratios of 35:1 and 351:1 where the cationic lipid finds its way to the surface of the particle in sufficient quantities to yield an overall net positive surface charge. This may suggest that at ratios as low as 351:1 in this particular formulation, excess DDAB that is not neutralized by DNA finds its way to the surface, giving the particles their positive charge.

Figure 3:
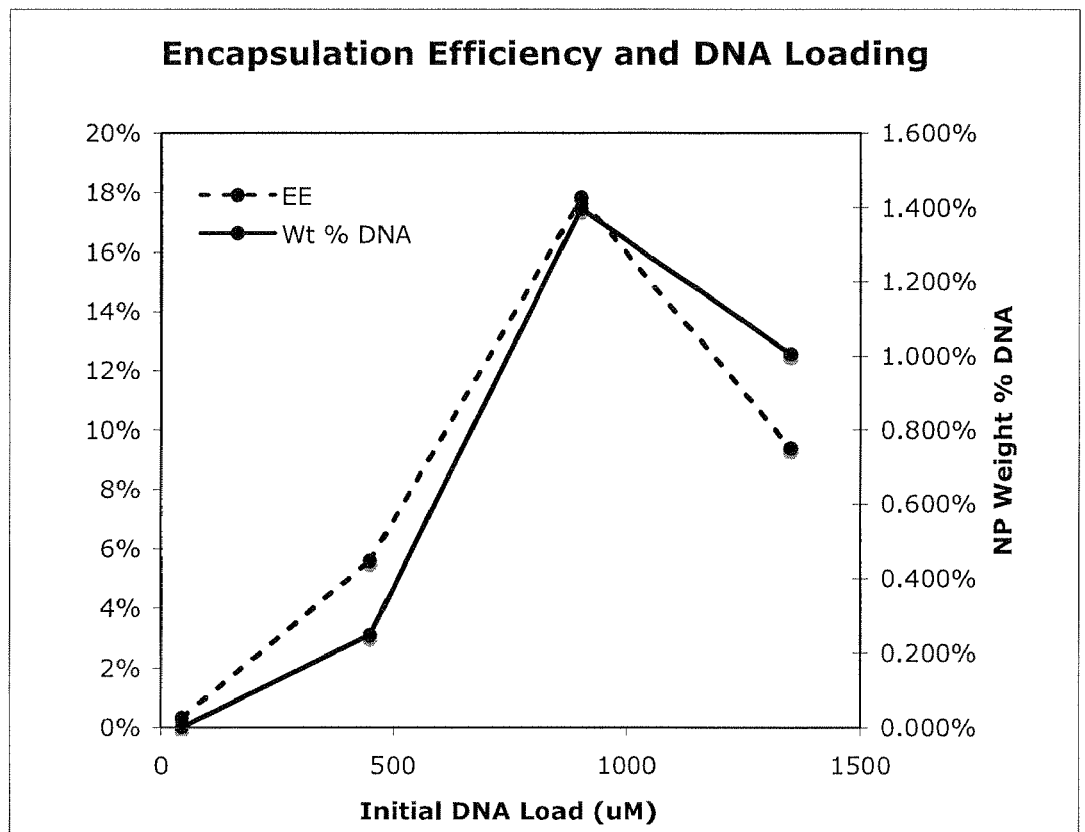
FIG. 3 demonstrates the effect of amphipathic lipid concentration on particle encapsulation efficiency.

FIG. 3 demonstrates the effect of amphipathic lipid concentration on particle encapsulation efficiency. Nanoparticles produced via the reverse micelle nanoprecipitation method are able to encapsulated up to ~18% of the initial load of 40 bp DNA in one study (represented by the dashed line; EE=mass DNA detected after particle lysis/initial mass of DNA). The encapsulated DNA in this case represents approximately 1.4% of the total initial mass of components used to formulate the nanoparticle (represented by the solid line; wt % DNA=mass DNA detected after particle lysis/total initial mass of polymer+lipid+DNA). Note that this represents the minimum expected numbers, since all of the components may not be represented in the same ratios in the nanoparticles as in the initial starting materials.

Figure 4:
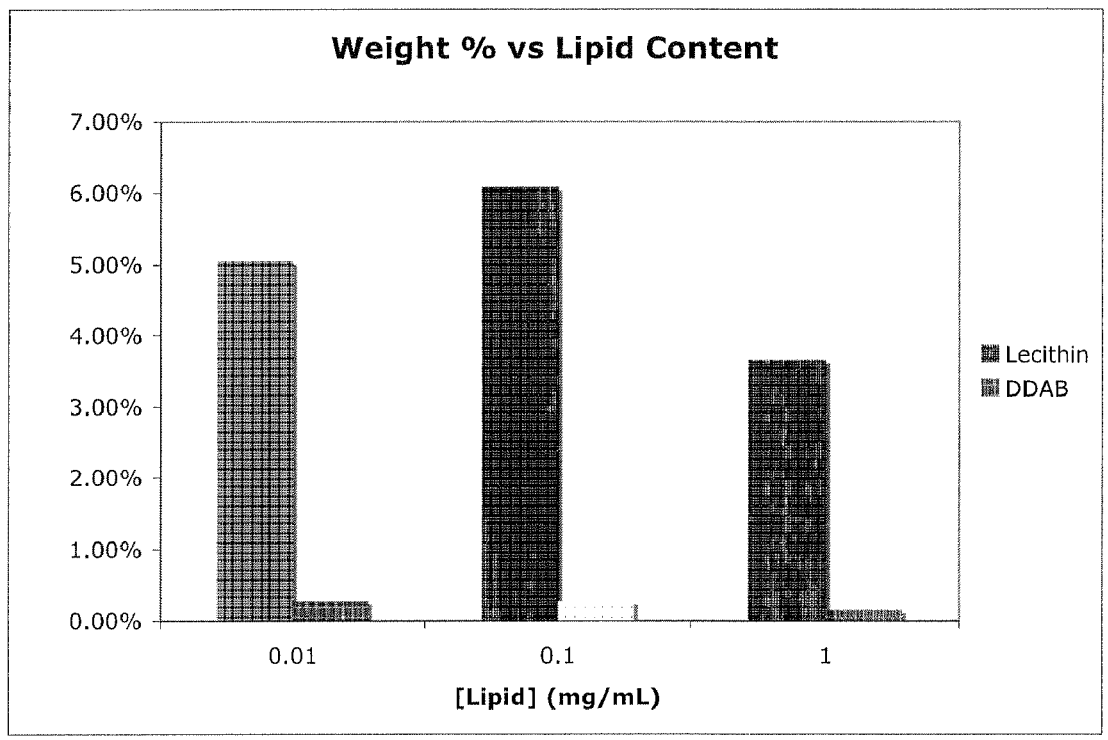
FIG. 4 demonstrates the effect of amphipathic lipid concentration on weight percent nucleic acids in the nanoparticles that are formed using the methods of the invention.

FIG. 4 demonstrates the effect of amphipathic lipid concentration on weight percent nucleic acids in the nanoparticles that are formed using the methods of the invention. In one study, the weight % (wt %) of DNA (40 bp double-stranded) in the nanoparticles (wt %=mass DNA detected after particle lysis/total initial mass polymer+lipid+DNA) varies with lipid concentration. Lecithin=neutral, DDAB (dimethyldioctadecyl ammonium bromide)=positively charged. Interestingly, use of the positively charged DDAB lipid results in much less DNA encapsulation.

Figure 5:
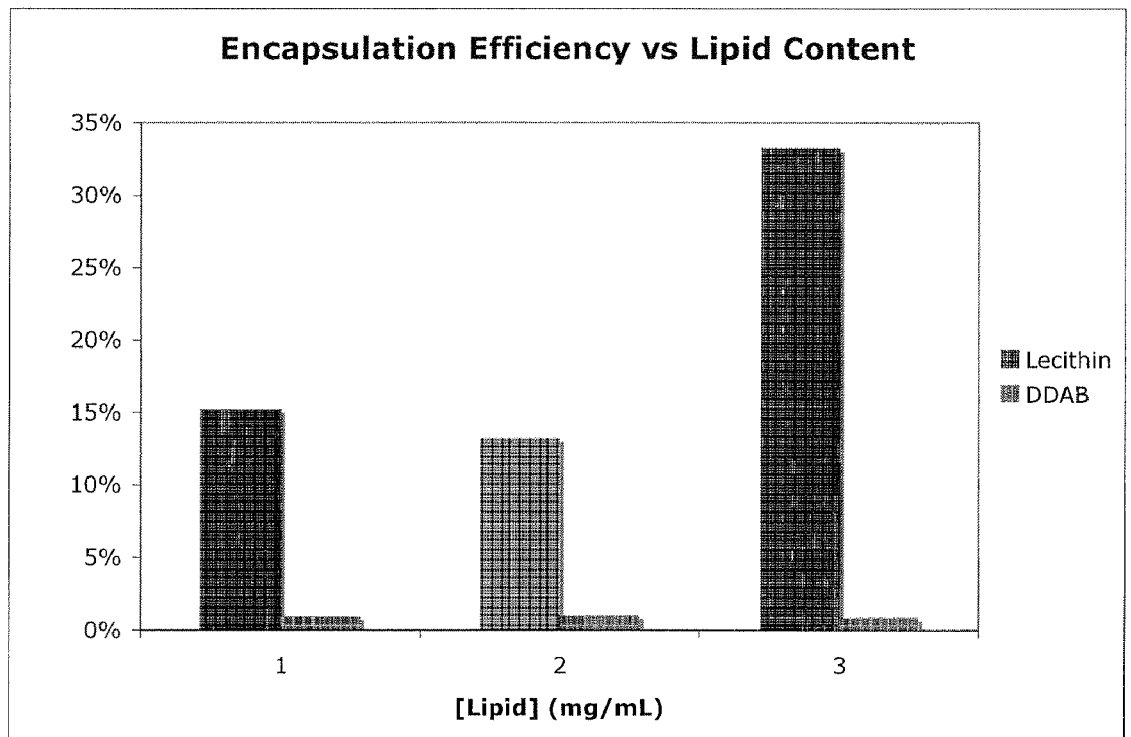
FIG. 5 demonstrates the effect of amphipathic lipid concentration on particle encapsulation efficiency.

FIG. 5 demonstrates the effect of amphipathic lipid concentration on particle encapsulation efficiency, using the same study described for FIG. 4. The encapsulation efficiency is correspondingly larger for lecithin nanoparticles as compared to DDAB, and was as high as approximately 30% in one case (3 mg/mL lipid in THF).

Figure 6:
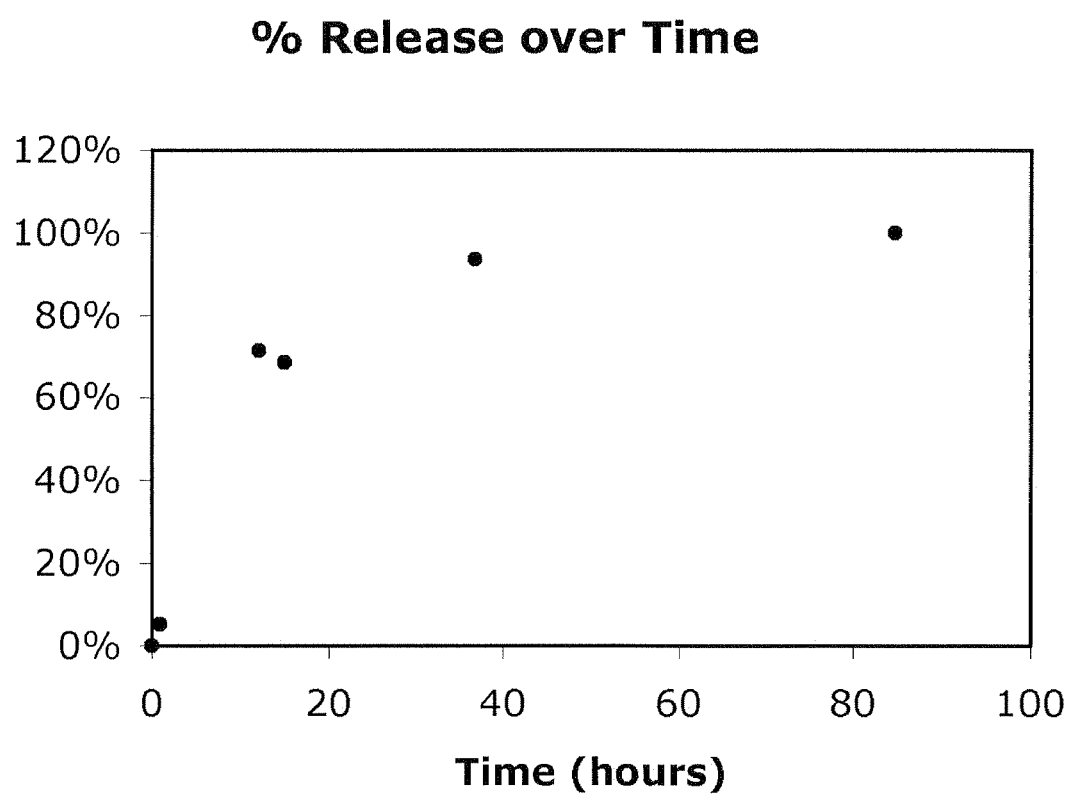
FIG. 6 demonstrates the effect of amphipathic lipid concentration on therapeutic agent release over time.

FIG. 6 demonstrates the effect of amphipathic lipid concentration on therapeutic agent release over time. A study of the release of 40 bp DNA from reverse micelle nanoparticles over time shows that approximately 50% of the encapsulated DNA is released within 5-10 hours, with complete release after approximately 40 hours.

Figure 7:
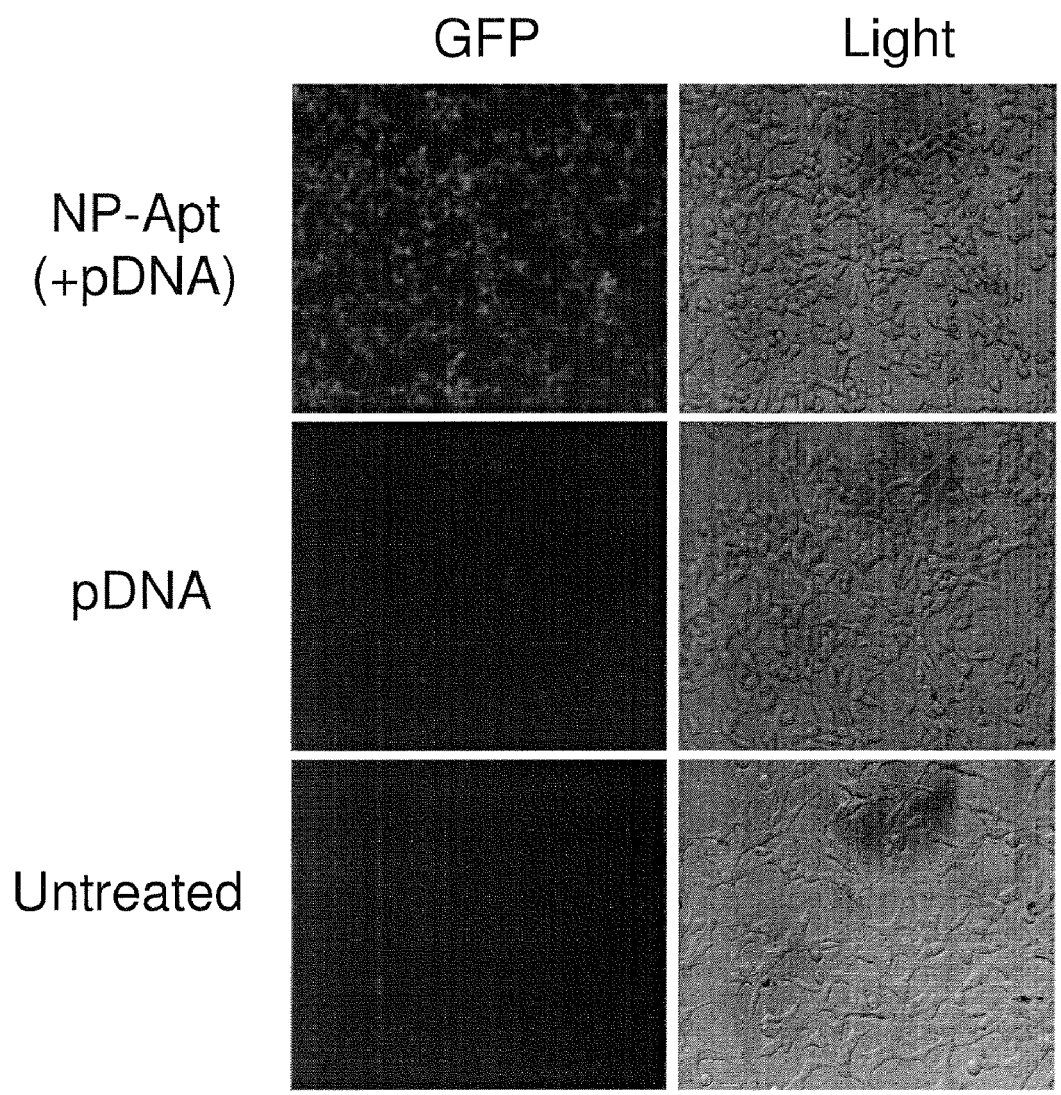
FIG. 7 demonstrates cell uptake of the polymer-encapsulated reverse micelles of the invention.

FIG. 7 demonstrates cell uptake of the polymer-encapsulated reverse micelles of the invention. Transfection of pCMV-GFP using reverse micelles encapsulated in 180 nm PLA-PEG nanoparticles. Aptamer targeted nanoparticles deliver plasmid DNA effectively, while controls do not.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

The invention claimed is:

1. Nanoparticles comprising reverse micelles encapsulating a hydrophilic nucleic acid or protein molecule, wherein the reverse micelles are encapsulated within a hydrophobic polymeric matrix.

2. The nanoparticles of claim 1, wherein targeting moieties are attached to the nanoparticle.

3. The nanoparticles of claim 2, wherein the targeting moiety is an aptamer.

4. The nanoparticles of claim 1, wherein the polymeric matrix comprises two or more polymers.

5. The nanoparticles of claim 1, wherein the polymeric matrix comprises a polymer selected from the group consisting of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, and combinations thereof.

6. The nanoparticles of claim 1, wherein the hydrophobic polymer forming the polymeric matrix comprises a polyalkylene glycol.

7. The nanoparticles of claim 1, wherein the polymeric matrix comprises poly(lactide-co-glycolide) (PLGA), polylactide (PLA), polyglycolide (PGA), or a polycaprolactone.

8. The nanoparticles of claim 1, wherein the polymeric matrix comprises a copolymer of two or more polymers.

9. The nanoparticles of claim 1, wherein the polymeric matrix comprises a lipid-terminated polyalkylene glycol and a polyester.

10. The nanoparticles of claim 9, wherein the polymeric matrix comprises lipid-terminated PEG and PLGA.

11. The nanoparticles of claim 10, wherein the lipid is of the Formula V

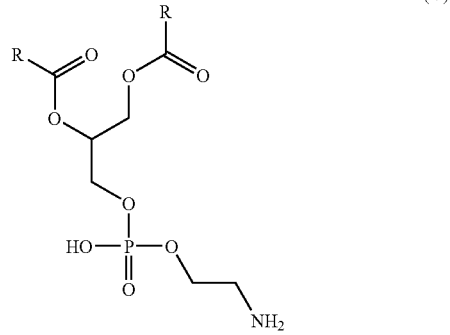

(V)

and salts thereof, wherein each R is, independently, $C_{1-30}$ alkyl.

12. The nanoparticles of claim 11, wherein the lipid is 1,2 distearoyl-sn-glycero-3-phosphoethanolamine (DSPE), and salts thereof.

13. The nanoparticles of claim 1, further comprising therapeutic, prophylactic or diagnostic agent encapsulated within the hydrophobic matrix of the nanoparticle.

14. The nanoparticles of claim 1, wherein the therapeutic agent is an siRNA.

15. The nanoparticles of claim 1, wherein the reverse micelle comprises an amphipathic lipid.

16. The nanoparticles of claim 15, wherein the amphipathic lipid is selected from the group consisting of lecithin, phosphatidylcholine, lipid A, cholesterol, dolichol, shingosine, sphingomyelin, ceramide, cerebroside, sulfatide, glycosylceramide, phytosphingosine, phosphatidylethanolamine, phosphatidylglycerol, phosphatidylinositol, phosphatidylserine, cardiolipin, phophatidic acid, and lysophophatides.

17. The nanoparticles of claim 16, wherein the therapeutic agent is a nucleic acid, and the ratio of amphipathic lipid to nucleic acid is approximately 33:1.

18. The nanoparticles of claim 2, wherein the targeting moiety binds prostate specific membrane antigen ("PSMA").

19. The nanoparticles of claim 18, wherein the targeting moiety binds PSMA on cells selected from the group consisting of prostate cancer, non-small cell lung cancer, colorectal carcinoma, and glioblastoma cells.

20. The nanoparticles of claim 1, wherein the therapeutic agent is a nucleic acid.

21. A pharmaceutical composition comprising the nanoparticles of claim 1 and a pharmaceutically acceptable excipient.

22. A method of preparing a nanoparticle of claim 1, the method comprising steps of
providing a hydrophilic therapeutic agent, diagnostic agent or prophylactic agent;
dissolving the agent with an amphipathic lipid in a volatile, water-miscible organic solvent;
forming reverse micelles, wherein the interior of the reverse micelle is hydrophilic and contains the therapeutic agent, diagnostic agent or prophylactic agent, and the exterior of the reverse micelle is hydrophobic;
adding a solution of a hydrophobic polymer to the mixture of reverse micelles;
combining the resulting mixture with a hydrophilic non-solvent that the polymer is not soluble in to form nanoparticle by rapid diffusion of the solvent into the non-solvent and evaporation of the solvent.

23. The nanoparticle formed by the method of claim 22.

24. The nanoparticles of claim 20, wherein the targeting moiety is an aptamer.

25. The nanoparticles of claim 2, wherein the nanoparticle has a cancer targeting moiety bound thereto.

* * * * *

```
                              SEQUENCE LISTING

<160> NUMBER OF SEQ ID NOS: 13

<210> SEQ ID NO 1
<211> LENGTH: 71
<212> TYPE: RNA
<213> ORGANISM: Artificial Sequence
<220> FEATURE:
<223> OTHER INFORMATION: Synthetic Oligonucleotide

<400> SEQUENCE: 1
gggaggacga ugcggaucag ccauguuuac gucacuccuu gucaauccuc aucggcagac      60
gacucgcccg a                                                          71

<210> SEQ ID NO 2
<211> LENGTH: 70
<212> TYPE: RNA
<213> ORGANISM: Artificial Sequence
<220> FEATURE:
<223> OTHER INFORMATION: Synthetic Oligonucleotide

<400> SEQUENCE: 2
gggaggacga ugcggaccga aaaagaccug acuucuauac uaagucuacg uucccagacg      60
acucgcccga                                                            70

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Ala Lys Glu Arg Cys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Cys Arg Glu Lys Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5
```

```
Ala Arg Tyr Leu Gln Lys Leu Asn
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (5)..(6)
<223> OTHER INFORMATION: any amino acid

<400> SEQUENCE: 6

Ala Xaa Tyr Leu Xaa Xaa Leu Asn
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ala Thr Trp Leu Pro Pro Arg
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Ala Cys Asp Cys Arg Gly Asp Cys Phe Cys Gly
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9

Cys Asn Gly Arg Cys
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

His Trp Gly Phe
1

<210> SEQ ID NO 11
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 11

Cys Thr Thr His Trp Gly Phe Thr Leu Cys
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Cys Gly Asn Lys Arg Thr Arg Gly Cys
1               5

<210> SEQ ID NO 13
<211> LENGTH: 19
<212> TYPE: RNA
<213> ORGANISM: Artificial Sequence
<220> FEATURE:
<223> OTHER INFORMATION: Synthetic nucleotide

<400> SEQUENCE: 13
gaaggccagu uguauggac                                              19
```